(12) United States Patent
Tuval et al.

(10) Patent No.: US 9,072,603 B2
(45) Date of Patent: Jul. 7, 2015

(54) MITRAL PROSTHESIS AND METHODS FOR IMPLANTATION

(75) Inventors: Yosi Tuval, Even Yehuda (IL); Ilia Hariton, Zichron Yaackov (IL); Igor Kovalsky, Givatamin (IL); Eli Ben-Hamou, Tel Aviv (IL)

(73) Assignee: Medtronic Ventor Technologies, Ltd., Minneapolis, MN (US)

( * ) Notice: Subject to any disclaimer, the term of this patent is extended or adjusted under 35 U.S.C. 154(b) by 838 days.

(21) Appl. No.: 12/914,678

(22) Filed: Oct. 28, 2010

(65) Prior Publication Data

US 2011/0208298 A1    Aug. 25, 2011

Related U.S. Application Data

(60) Provisional application No. 61/307,743, filed on Feb. 24, 2010.

(51) Int. Cl.
*A61F 2/24* (2006.01)

(52) U.S. Cl.
CPC ............. *A61F 2/2418* (2013.01); *A61F 2/2436* (2013.01); *A61F 2250/0039* (2013.01); *A61F 2250/006* (2013.01); *A61F 2220/0008* (2013.01); *A61F 2220/0016* (2013.01); *A61F 2220/0075* (2013.01); *A61F 2230/0013* (2013.01); *A61F 2230/005* (2013.01); *A61F 2230/008* (2013.01)

(58) Field of Classification Search
CPC ....... A61F 2/24; A61F 2/2463; A61F 2/2442; A61F 2/2475; A61F 2/2451; A61F 2/2469
USPC ............................... 623/1.24, 1.31, 2.17, 1.26
See application file for complete search history.

(56) References Cited

U.S. PATENT DOCUMENTS

| 6,059,715 | A | 5/2000 | Schweich, Jr. et al. |
|---|---|---|---|
| 6,210,432 | B1 | 4/2001 | Salem |
| 6,332,893 | B1 | 12/2001 | Mortier |
| 6,425,916 | B1 * | 7/2002 | Garrison et al. ............. 623/2.11 |
| 6,491,707 | B2 | 12/2002 | Makower et al. |
| 6,602,288 | B1 | 8/2003 | Cosgrove |
| 6,676,698 | B2 * | 1/2004 | McGuckin et al. .......... 623/1.24 |
| 6,702,835 | B2 | 3/2004 | Ginn |
| 6,723,038 | B1 | 4/2004 | Schroeder |

(Continued)

FOREIGN PATENT DOCUMENTS

| WO | 2004/019825 | 3/2004 |
|---|---|---|
| WO | WO2005/027797 | 3/2005 |

(Continued)

*Primary Examiner* — Thomas J Sweet
*Assistant Examiner* — Seema Mathew

(57) ABSTRACT

Apparatus and methods are provided, including a mitral valve prosthesis for implantation at a native mitral valve complex of a subject. The prosthesis includes an inner support structure having a downstream section, and an upstream section, the upstream section having a cross-sectional area greater than the downstream section, the inner support structure being configured to be positioned at least partially on an atrial side of the native valve complex, and to apply an axial force directed toward a left ventricle. The prosthesis further includes an outer support structure having two or more engagement arms, the engagement arms being coupled to the inner support structure. The prosthesis is configured, upon implantation thereof, to clamp portions of leaflets of the native valve between the inner support structure and the engagement arms. Other embodiments are also described.

36 Claims, 47 Drawing Sheets

(56) References Cited

U.S. PATENT DOCUMENTS

| | | | |
|---|---|---|---|
| 6,776,784 B2 | 8/2004 | Ginn | |
| 6,962,605 B2 | 11/2005 | Cosgrove | |
| 6,986,775 B2 | 1/2006 | Morales | |
| 6,989,028 B2 | 1/2006 | Lashinski | |
| 6,997,950 B2 | 2/2006 | Chawla | |
| 6,997,951 B2 | 2/2006 | Solem | |
| 7,011,682 B2 | 3/2006 | Lashinski | |
| 7,037,334 B1 | 5/2006 | Hlavka | |
| 7,044,967 B1 | 5/2006 | Solem | |
| 7,056,325 B1 | 6/2006 | Makower | |
| 7,090,695 B2 | 8/2006 | Solem | |
| 7,166,127 B2 | 1/2007 | Spence | |
| 7,201,772 B2 * | 4/2007 | Schwammenthal et al. | 623/2.18 |
| 7,211,110 B2 | 5/2007 | Rowe | |
| 7,220,265 B2 | 5/2007 | Chanduszko | |
| 7,296,577 B2 | 11/2007 | Lashinski | |
| 7,311,728 B2 | 12/2007 | Solem | |
| 7,431,692 B2 | 10/2008 | Zollinger | |
| 7,431,726 B2 | 10/2008 | Spence | |
| 7,588,582 B2 | 9/2009 | Starksen | |
| 7,635,386 B1 | 12/2009 | Gammie | |
| 7,637,945 B2 | 12/2009 | Solem | |
| 7,666,193 B2 | 2/2010 | Starksen | |
| 7,717,954 B2 | 5/2010 | Solem | |
| 7,744,611 B2 | 6/2010 | Nguyen et al. | |
| 7,753,922 B2 | 7/2010 | Starksen | |
| 7,758,637 B2 | 7/2010 | Starksen | |
| 7,871,436 B2 * | 1/2011 | Ryan et al. | 623/2.17 |
| 8,092,520 B2 * | 1/2012 | Quadri | 623/1.36 |
| 8,257,429 B2 * | 9/2012 | Pavcnik | 623/1.24 |
| 8,308,798 B2 * | 11/2012 | Pintor et al. | 623/2.18 |
| 8,366,767 B2 * | 2/2013 | Zhang | 623/2.11 |
| 8,591,570 B2 * | 11/2013 | Revuelta et al. | 623/1.26 |
| 8,652,203 B2 * | 2/2014 | Quadri et al. | 623/2.11 |
| 8,747,458 B2 * | 6/2014 | Tuval et al. | 623/2.11 |
| 8,852,272 B2 * | 10/2014 | Gross et al. | 623/2.18 |
| 8,926,690 B2 * | 1/2015 | Kovalsky | 623/1.26 |
| 8,951,223 B2 * | 2/2015 | McNamara et al. | 604/8 |
| 2003/0036791 A1 * | 2/2003 | Philipp et al. | 623/1.11 |
| 2003/0105519 A1 | 6/2003 | Fasol | |
| 2003/0149478 A1 * | 8/2003 | Figulla et al. | 623/2.38 |
| 2004/0050393 A1 | 3/2004 | Golden et al. | |
| 2004/0092858 A1 * | 5/2004 | Wilson et al. | 604/9 |
| 2004/0193191 A1 | 9/2004 | Starksen | |
| 2004/0220596 A1 | 11/2004 | Frazier | |
| 2004/0243227 A1 | 12/2004 | Starksen | |
| 2005/0107810 A1 | 5/2005 | Morales | |
| 2005/0107811 A1 | 5/2005 | Starksen | |
| 2005/0107812 A1 | 5/2005 | Starksen | |
| 2005/0177180 A1 | 8/2005 | Kaganov | |
| 2005/0187568 A1 | 8/2005 | Klenk | |
| 2005/0197696 A1 | 9/2005 | Duran | |
| 2005/0267495 A1 | 12/2005 | Ginn | |
| 2005/0273138 A1 | 12/2005 | To | |
| 2006/0025787 A1 | 2/2006 | Morales | |
| 2006/0052821 A1 | 3/2006 | Abbott | |
| 2006/0058872 A1 | 3/2006 | Salahieh et al. | |
| 2006/0095025 A1 | 5/2006 | Levine | |
| 2006/0259135 A1 * | 11/2006 | Navia et al. | 623/2.11 |
| 2007/0010857 A1 | 1/2007 | Sugimoto | |
| 2007/0055206 A1 | 3/2007 | To | |
| 2007/0073315 A1 | 3/2007 | Ginn | |
| 2007/0112424 A1 | 5/2007 | Spence | |
| 2007/0232992 A1 * | 10/2007 | Kutsko et al. | 604/30 |
| 2008/0071361 A1 | 3/2008 | Tuval | |
| 2008/0071362 A1 | 3/2008 | Tuval | |
| 2008/0071363 A1 | 3/2008 | Tuval | |
| 2008/0071366 A1 | 3/2008 | Tuval | |
| 2008/0071368 A1 | 3/2008 | Tuval | |
| 2008/0071369 A1 | 3/2008 | Tuval | |
| 2008/0082166 A1 * | 4/2008 | Styrc et al. | 623/2.18 |
| 2008/0208328 A1 | 8/2008 | Antocci | |
| 2008/0228032 A1 | 9/2008 | Starksen | |
| 2008/0228165 A1 | 9/2008 | Spence | |
| 2008/0228265 A1 | 9/2008 | Spence | |
| 2008/0228266 A1 | 9/2008 | McNamara | |
| 2008/0228267 A1 | 9/2008 | Spence | |
| 2008/0234701 A1 | 9/2008 | Morales | |
| 2008/0234702 A1 | 9/2008 | Morales | |
| 2008/0234704 A1 | 9/2008 | Starksen | |
| 2008/0234728 A1 | 9/2008 | Starksen | |
| 2008/0234815 A1 | 9/2008 | Starksen | |
| 2008/0243150 A1 | 10/2008 | Starksen | |
| 2008/0255660 A1 | 10/2008 | Guyenot | |
| 2008/0255661 A1 | 10/2008 | Straubinger | |
| 2008/0275503 A1 | 11/2008 | Spence | |
| 2009/0005863 A1 * | 1/2009 | Goetz et al. | 623/2.18 |
| 2009/0062901 A1 * | 3/2009 | McGuckin, Jr. | 623/1.15 |
| 2009/0076547 A1 | 3/2009 | Sugimoto | |
| 2009/0112309 A1 * | 4/2009 | Jaramillo et al. | 623/1.26 |
| 2009/0209950 A1 | 8/2009 | Starksen | |
| 2009/0216310 A1 | 8/2009 | Straubinger | |
| 2009/0216312 A1 | 8/2009 | Straubinger | |
| 2009/0216313 A1 | 8/2009 | Straubinger | |
| 2009/0222083 A1 | 9/2009 | Nguyen | |
| 2009/0234318 A1 | 9/2009 | Loulmet | |
| 2009/0276040 A1 | 11/2009 | Rowe | |
| 2009/0287299 A1 * | 11/2009 | Tabor et al. | 623/1.26 |
| 2010/0023056 A1 | 1/2010 | Johansson | |
| 2010/0030330 A1 | 2/2010 | Bobo | |
| 2010/0070028 A1 | 3/2010 | Sugimoto | |
| 2010/0161042 A1 | 6/2010 | Maisano | |
| 2010/0217382 A1 | 8/2010 | Chau | |
| 2010/0298931 A1 * | 11/2010 | Quadri et al. | 623/2.11 |
| 2011/0022157 A1 * | 1/2011 | Essinger et al. | 623/1.26 |
| 2011/0029072 A1 * | 2/2011 | Gabbay | 623/2.23 |
| 2011/0137397 A1 * | 6/2011 | Chau et al. | 623/1.11 |
| 2011/0224785 A1 * | 9/2011 | Hacohen | 623/2.18 |
| 2011/0257723 A1 * | 10/2011 | McNamara | 623/1.11 |
| 2011/0264196 A1 * | 10/2011 | Savage et al. | 623/1.26 |
| 2011/0319988 A1 * | 12/2011 | Schankereli et al. | 623/2.11 |
| 2012/0022640 A1 * | 1/2012 | Gross et al. | 623/2.11 |
| 2012/0053685 A1 * | 3/2012 | Cerf et al. | 623/2.17 |
| 2012/0078347 A1 * | 3/2012 | Braido et al. | 623/1.26 |
| 2012/0078360 A1 * | 3/2012 | Rafiee | 623/2.37 |
| 2014/0018906 A1 * | 1/2014 | Rafiee | 623/1.26 |
| 2014/0067048 A1 * | 3/2014 | Chau et al. | 623/2.1 |
| 2014/0067054 A1 * | 3/2014 | Chau et al. | 623/2.36 |
| 2014/0135908 A1 * | 5/2014 | Glozman et al. | 623/2.11 |
| 2014/0222136 A1 * | 8/2014 | Geist et al. | 623/2.11 |
| 2014/0243966 A1 * | 8/2014 | Garde et al. | 623/2.18 |
| 2014/0277390 A1 * | 9/2014 | Ratz et al. | 623/1.26 |
| 2014/0277427 A1 * | 9/2014 | Ratz et al. | 623/2.38 |
| 2014/0316516 A1 * | 10/2014 | Vidlund et al. | 623/2.1 |

FOREIGN PATENT DOCUMENTS

| | | |
|---|---|---|
| WO | 2008/129405 | 10/2008 |
| WO | WO2009/053497 | 4/2009 |
| WO | WO2009/132187 | 10/2009 |
| WO | WO2010/098857 | 9/2010 |
| WO | WO2010/117680 | 10/2010 |

* cited by examiner

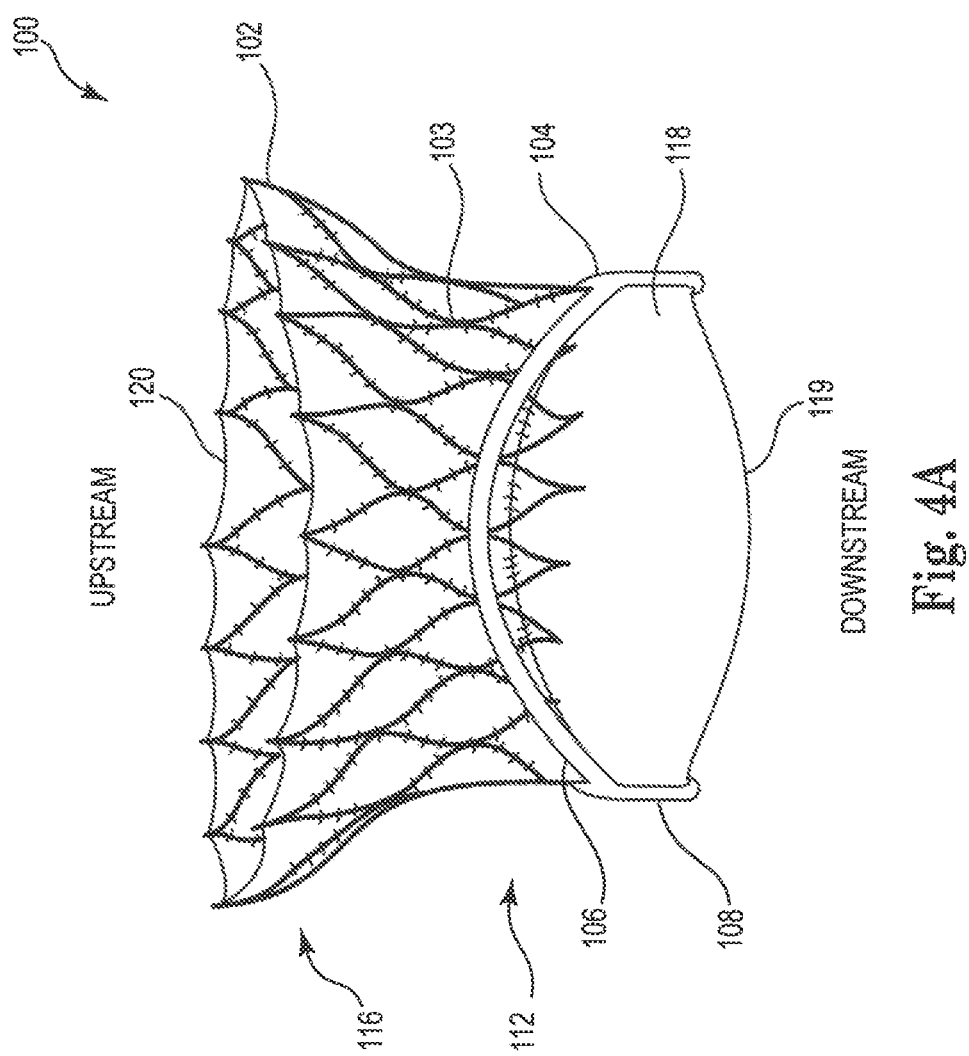

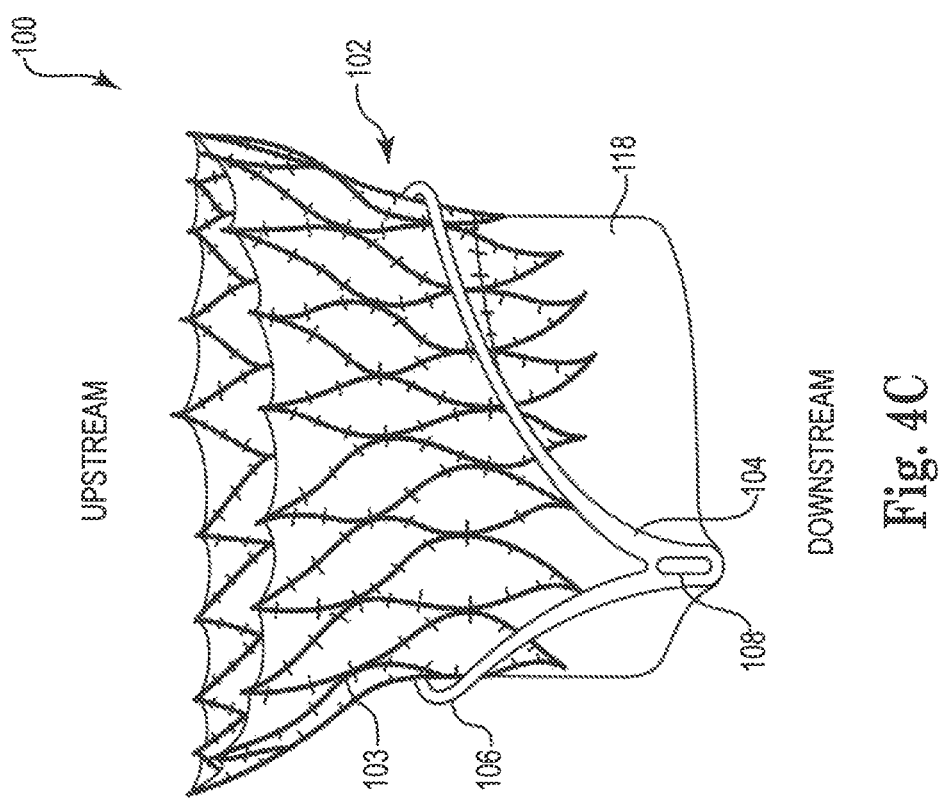

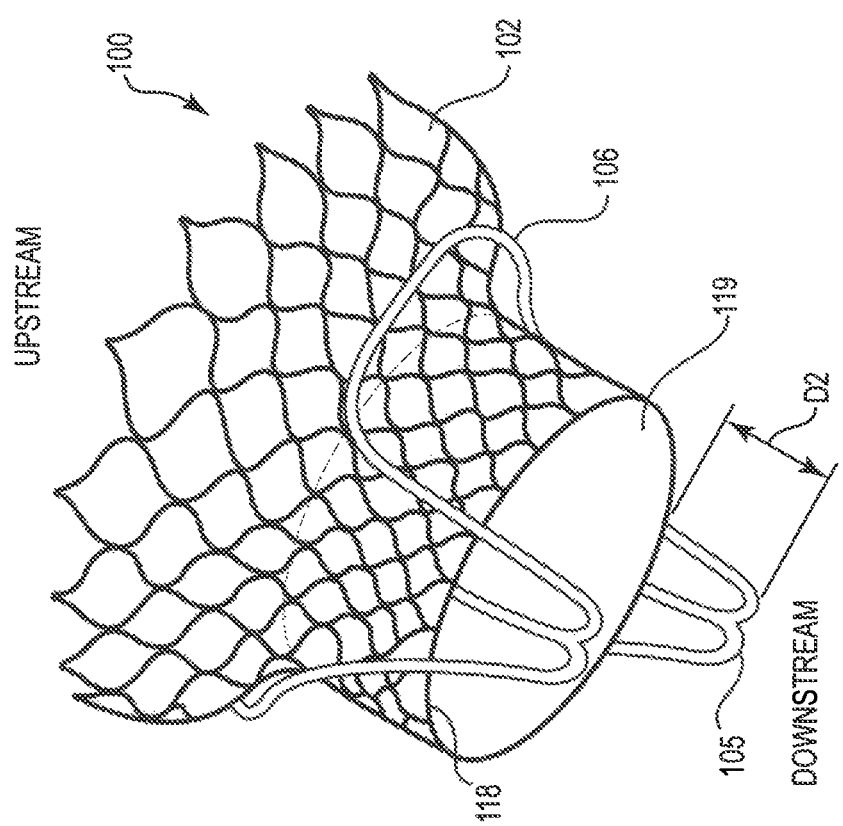

UPSTREAM

DOWNSTREAM

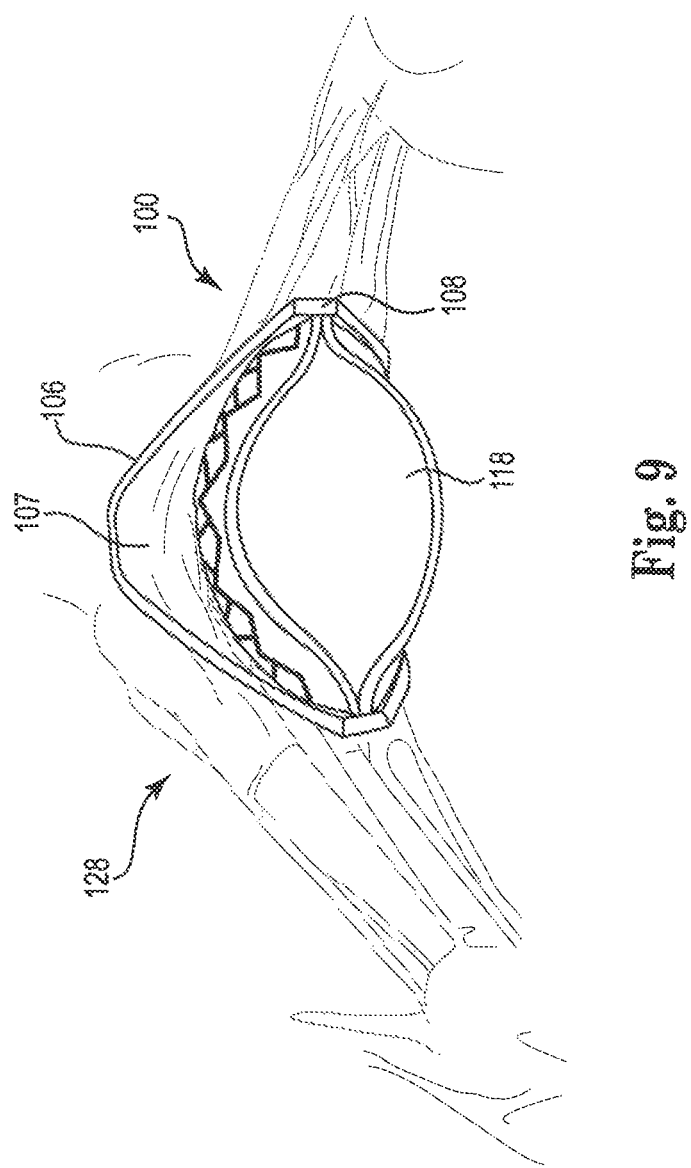

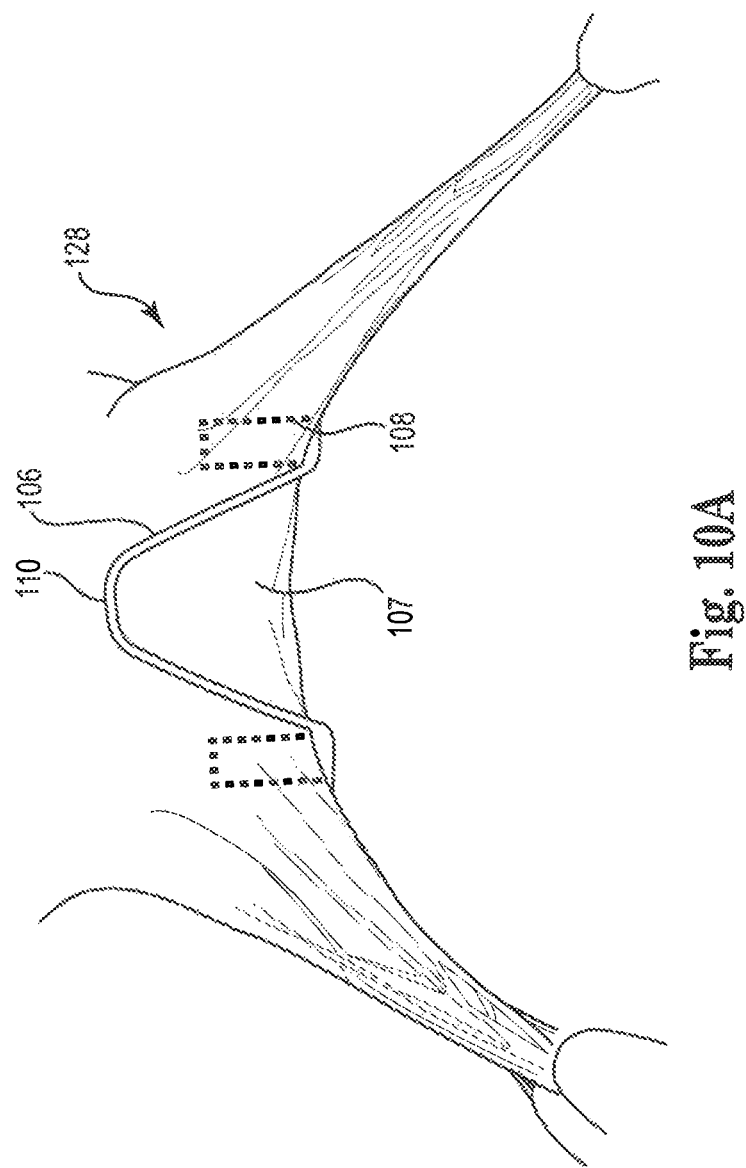

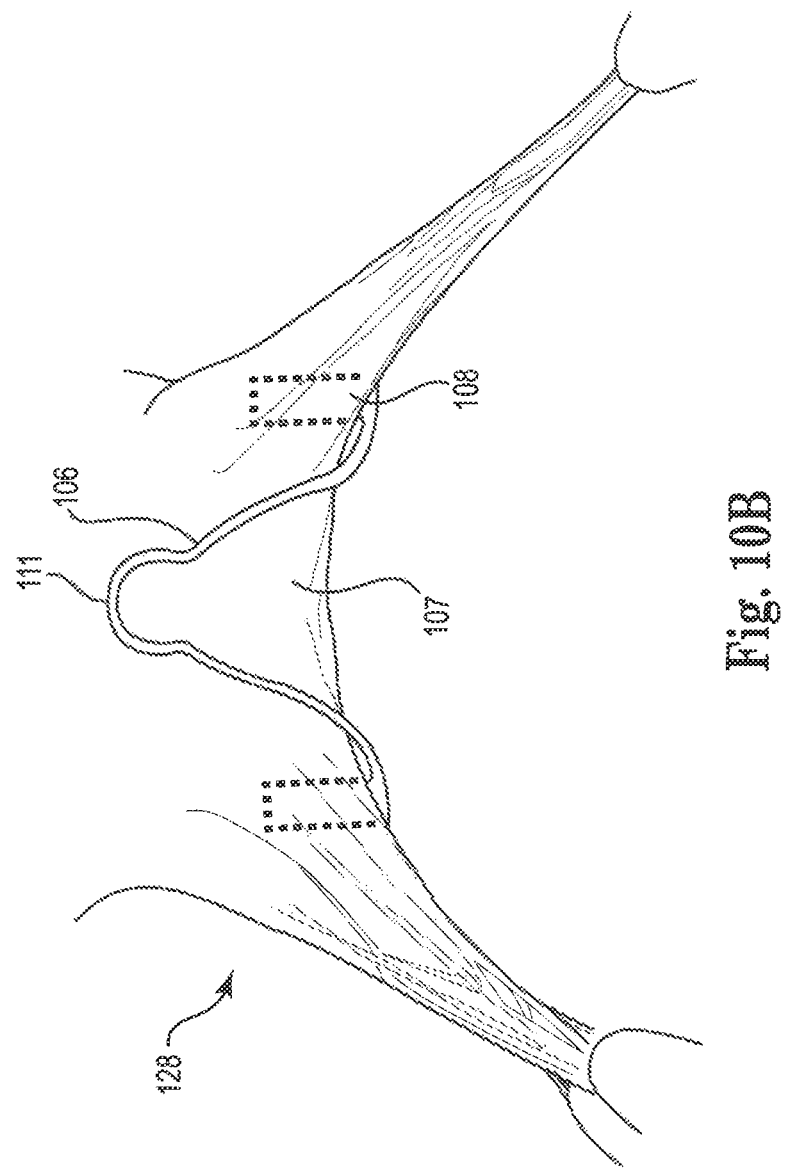

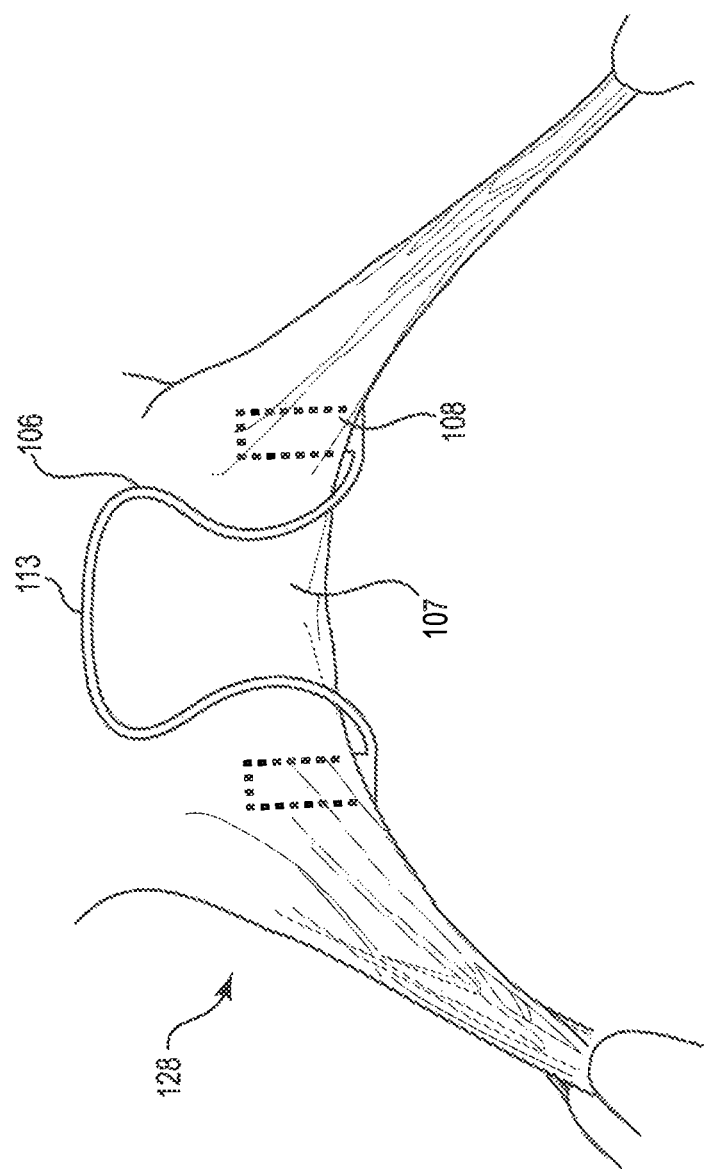

MITRAL PROSTHESIS AND METHODS FOR IMPLANTATION

CROSS REFERENCES TO RELATED APPLICATIONS

The present application claims the benefit of U.S. Provisional Application 61/307,743, filed Feb. 24, 2010, entitled, "Mitral prosthesis and methods for implantation," which is incorporated herein by reference.

FIELD OF EMBODIMENTS OF THE INVENTION

Some applications of the present invention generally relate to implantable medical apparatus. Specifically, some applications of the present invention relate to apparatus and methods associated with prosthetic heart valves.

BACKGROUND

The mitral valve exhibits two types of pathologies: regurgitation and stenosis. Regurgitation is the more common of the two defects. Either defect may be treated by surgical repair. Under certain conditions, the mitral valve must be replaced. Standard approaches to mitral valve replacement require cutting open the left side of the heart to access the native mitral valve.

US 2008/0071368 to Tuval describes a prosthesis for implantation at a native semilunar valve of a native valve complex. The prosthesis includes a distal fixation member, configured to be positioned in a downstream artery, and shaped so as to define exactly three proximal engagement arms that are configured to be positioned at least partially within respective ones of semilunar sinuses, and, in combination, to apply, to tissue that defines the semilunar sinuses, a first axial force directed toward a ventricle. The prosthesis further includes a proximal fixation member coupled to the distal fixation member, the proximal fixation member configured to be positioned at least partially on a ventricular side of the native semilunar valve, and to apply, to the ventricular side of the native valve complex, a second axial force directed toward the downstream artery, such that application of the first and second forces couples the prosthesis to the native valve complex.

US 2009/0276040 to Rowe describes a prosthetic mitral valve assembly and method of inserting the same. In certain embodiments, the prosthetic mitral valve assembly has a flared upper end and a tapered portion to fit the contours of the native mitral valve. The prosthetic mitral valve assembly can include a stent or outer support frame with a valve mounted therein. The assembly is described as being adapted to expand radially outwardly and into contact with the native tissue to create a pressure fit. One embodiment is described including positioning the mitral valve assembly below the annulus such that the annulus itself can restrict the assembly from moving in an upward direction towards the left atrium. The mitral valve assembly is also described as being positioned so that the leaflets of the mitral valve hold the assembly to prevent downward movement of the assembly towards the left ventricle.

US 2010/0217382 to Chau describes a prosthetic mitral valve assembly and method of inserting the same. In certain embodiments, the prosthetic mitral valve assembly includes a stent and valve combination. The stent is designed so that the anchoring portion is positioned above the annulus of the mitral valve and in the left atrium. The stent is radially expandable so that it can expand into position against the walls of the left atrium and accommodate a wide range of anatomies. Contact between the stent and the native tissue in the left atrium is described as reducing paravalvular leakage and preventing migration of the stent once in place.

US 2009/0005863 to Goetz describes a replacement valve for implantation centrally within the orifice of a malfunctioning native heart valve. The valve is designed for minimally invasive entry through an intercostal opening in the chest of a patient and an opening in the apex of the human heart. The replacement valve includes either a separate anchor or a combined anchor that folds around the malfunctioning native valve leaflets, sandwiching them in a manner so as to securely anchor the replacement valve in a precise, desired location.

US 2009/0216312 to Straubinger describes a stent for the positioning and anchoring of a valvular prosthesis in an implantation site in the heart of a patient. Specifically, the Straubinger application relates to an expandable stent for an endoprosthesis used in the treatment of a narrowing of a cardiac valve and/or a cardiac valve insufficiency. The stent is described as comprising at least one fastening portion via which the valvular prosthesis is connectable to the stent, so as to ensure that no longitudinal displacement of a valvular prosthesis fastened to a stent will occur relative the stent in the implanted state of the stent, even given the peristaltic motion of the heart. The stent further comprises positioning arches and retaining arches, whereby at least one positioning arch is connected to at least one retaining arch via a first connecting web. The stent moreover comprises at least one auxiliary retaining arch which connects the respective arms of the at least one retaining arch connected to the at least one positioning arch.

US 2008/0255660 to Guyenot describes a medical device for treating a heart valve insufficiency, with an endoprosthesis which can be introduced into a patient's body and expanded to secure a heart valve prosthesis in the patient's aorta. In an embodiment, the endoprosthesis has a plurality of positioning arches configured to be positioned with respect to a patient's aorta and a plurality of retaining arches to support a heart valve prosthesis. The endoprosthesis includes a first collapsed mode during the process of introducing it into the patient's body and a second expanded mode when it is implanted.

The following references may be of interest:
US 2010/0030330 to Bobo
US 2009/0216313 to Straubinger
US 2009/0216310 to Straubinger
US 2008/0255661 to Straubinger
US 2008/0208328 to Antocci
US 2008/0071369 to Tuval
US 2008/0071363 to Tuval
US 2008/0071366 to Tuval
US 2008/0071362 to Tuval
US 2008/0071361 to Tuval
US 2003/0036791 to Bonhoeffer
WO 04/019825 to Figulla

SUMMARY OF EMBODIMENTS

For some applications of the present invention, mitral valve prostheses and methods for implanting the prostheses are provided. The prostheses are typically implanted transcatheterally, for example, transapically (i.e., through the apex of the heart), transatrially (i.e., through the left atrium of the heart), and/or transseptally (i.e., through the septum of the heart). The prostheses typically include inner and outer support structures, the outer support structure including engagement arms. A valve prosthesis is typically sutured to the inner support structure.

Typically, the prostheses are placed on the native mitral valve complex such that the native leaflets are clamped between the inner support structure and the engagement arms. For some applications, such a configuration prevents the native leaflets from obstructing flow through the left ventricular outflow tract (LVOT), prevents the native leaflets from interacting with the prosthetic leaflets, recruits the native leaflets in minimizing peri-valvular leaks, maintains proper alignment of the valve prosthesis, avoids systolic anterior mobility, and/or maintains valve stability by preventing migration of the valve into the atrium or ventricle. For some applications, the design of the prosthesis is similar to the native valve and supports a non-round in vivo configuration, which reflects native valve function.

There is therefore provided, in accordance with some applications of the present invention, apparatus including a mitral valve prosthesis for implantation at a native mitral valve complex of a subject, the prosthesis including:

an inner support structure having a downstream section, and an upstream section, the upstream section having a cross-sectional area greater than the downstream section, the inner support structure being configured to be positioned at least partially on an atrial side of the native valve complex, and to apply an axial force directed toward a left ventricle; and an outer support structure having two or more engagement arms, the engagement arms being coupled to the inner support structure, the prosthesis being configured, upon implantation thereof, to clamp portions of leaflets of the native valve between the inner support structure and the engagement arms.

For some applications, the engagement arms are integrally formed with the inner support structure.

For some applications, the engagement arms include posterior and anterior engagement arms configured to clamp, respectively, posterior and anterior leaflets of the native mitral valve complex, and a ratio of a length of the anterior engagement arm to a length of the posterior arm is between 1.1:1 and 15:1.

For some applications, the ratio is between 1.3:1 and 2:1.

For some applications, the length of the anterior engagement arm is between 2 mm and 35 mm.

For some applications, the length of the anterior engagement arm is between 15 mm and 25 mm.

For some applications, the length of the posterior engagement arm is between 2 mm and 35 mm.

For some applications, the length of the posterior engagement arm is between 7 mm and 23 mm.

For some applications, the outer support structure further includes a connecting frame, the connecting frame of the outer support structure being configured to be coupled to the inner support structure.

For some applications, the inner support structure is shaped to define a plurality of cells, and the connecting frame of the outer support structure is shaped to define a plurality of cells having shapes and sizes that match cells of the inner support structure.

For some applications, the prosthesis is configured, upon implantation thereof, to reduce motion of native valve leaflets, by clamping portions of leaflets of the native valve between the inner support structure and the engagement arms.

For some applications, the prosthesis is configured to immobilize the native valve leaflets, by clamping the leaflets inside the engagement arms.

For some applications, the prosthesis is configured to prevent systolic anterior motion of the native valve leaflets, by clamping the leaflets inside the engagement arms.

For some applications, the prosthesis is configured to prevent the native leaflets from interfering with LVOT, by clamping the leaflets inside the engagement arms.

For some applications, the outer support structure further includes covers for covering the engagement arms, the covers being configured to reduce the motion of the native leaflets.

For some applications, the apparatus further includes a prosthetic valve that includes prosthetic valve leaflets and that is coupled to the inner support structure, the prosthesis being configured such that, upon implantation thereof:

downstream ends of native valve leaflets of the native mitral valve complex, downstream ends of the engagement arms, and downstream ends of the prosthetic leaflets, are disposed at a longitudinal distance from one another of less than 3 mm, the longitudinal distance being measured in a direction of a longitudinal axis of the prosthesis.

For some applications, the downstream ends of the engagement arms are coupled to the inner support structure within 3 mm of a downstream end of the inner support structure.

For some applications, the prosthesis is configured such that, upon implantation thereof, no portion of the prosthesis protrudes into a left ventricle of the subject by more than 3 mm.

For some applications, the prosthesis is configured such that, upon implantation thereof:

the downstream ends of native valve leaflets of the native mitral valve complex, the downstream ends of the engagement arms, and the downstream ends of the prosthetic leaflets, are disposed at a longitudinal distance from one another of less than 1 mm, the longitudinal distance being measured in a direction of a longitudinal axis of the prosthesis.

For some applications, the prosthesis is configured such that, upon implantation thereof, no portion of the prosthesis protrudes into a left ventricle of the subject by more than 1 mm.

For some applications, the downstream ends of the engagement arms are coupled to the inner support structure within 1 mm of a downstream end of the inner support structure.

For some applications, the engagement arms are configured to define first configurations thereof during implantation of the prosthesis, and to change shape so as to define second configurations thereof, subsequent to being placed over the native leaflets of the native mitral valve complex, each of the engagement arms spanning a width of less than 12 mm in the first configuration thereof, and spanning a width of more than 15 mm when in the second configuration thereof.

For some applications, in the first configuration thereof, the engagement arms are configured to facilitate functioning of the native valve complex during implantation of the prosthesis.

For some applications, in the first configuration thereof, the engagement arms are configured to fit between papillary muscles of the native valve complex.

For some applications, in the first configuration thereof, the engagement arms are configured to span a width of less than 8 mm.

For some applications, in the second configuration thereof, the engagement arms are configured to span a width of more than 35 mm.

For some applications, the apparatus further includes a prosthetic valve having prosthetic valve leaflets coupled to the inner support structure such that downstream ends of the prosthetic valve leaflets are within 3 mm of the downstream ends of the engagement arms, the engagement arms are coupled to the inner support structure at downstream ends of the engagement arms, and a longitudinal distance from a downstream end to an upstream end of each of the engagement arms is less than 18 mm, the longitudinal distance being measured in a direction of a longitudinal axis of the prosthesis.

For some applications, the prosthetic valve leaflets are coupled to the inner support structure such that downstream ends of the prosthetic valve leaflets are within 1 mm of the downstream ends of the engagement arms.

For some applications, the downstream ends of the engagement arms are coupled to the inner support structure within 3 mm of a downstream end of the inner support structure.

For some applications, the downstream ends of the engagement arms are coupled to the inner support structure within 1 mm of a downstream end of the inner support structure.

For some applications, the longitudinal distance from the downstream end to the upstream end of each of the engagement arms is less than 12 mm.

For some applications, the longitudinal distance from the downstream end to the upstream end of each of the engagement arms is less than 10 mm.

For some applications, the apparatus further includes a prosthetic valve having prosthetic valve leaflets coupled to the inner support structure, the prosthesis being configured such that, upon implantation thereof:

downstream ends of native valve leaflets of the native mitral valve complex, and downstream ends of the engagement arms are disposed at a longitudinal distance from one another of less than 3 mm, the longitudinal distance being measured in a direction of a longitudinal axis of the prosthesis, and a downstream end of the inner support structure and downstream ends of the prosthetic valve leaflets are at a longitudinal distance of at least 4 mm upstream of the downstream ends of the native valve leaflets, the longitudinal distance being measured in a direction of a longitudinal axis of the prosthesis.

For some applications, the prosthesis is configured such that, upon implantation thereof, the downstream end of the inner support structure and the downstream ends of the prosthetic valve leaflets are at a longitudinal distance of at least 10 mm upstream of the downstream ends of the native valve leaflets.

For some applications, the apparatus further includes a prosthetic valve having prosthetic valve leaflets, the prosthetic valve leaflets being coupled to the inner support structure such that downstream ends of the prosthetic valve leaflets are at least 4 mm upstream of the downstream ends of the engagement arms.

For some applications, the prosthetic valve leaflets are coupled to the inner support structure such that the downstream ends of the prosthetic valve leaflets are at least 10 mm upstream of the downstream ends of the engagement arms.

The present invention will be more fully understood from the following detailed description of embodiments thereof, taken together with the drawings, in which:

BRIEF DESCRIPTION OF THE DRAWINGS

FIGS. 4A-F are schematic illustrations of mitral prostheses, in accordance with some applications of the present invention;

FIG. 9 is a schematic illustration of an implanted mitral valve prosthesis, in accordance with some applications of the present invention;

FIGS. 10A-D are schematic illustrations of the engagement arms of the mitral valve prosthesis, in accordance with respective applications of the present invention;

DETAILED DESCRIPTION OF EMBODIMENTS

Figure 1A:
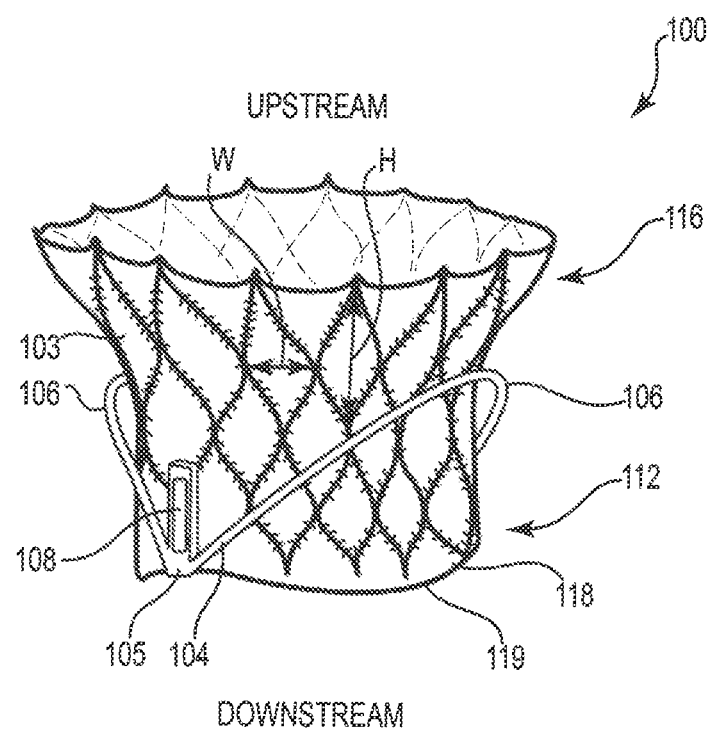
FIGS. 1A-D are schematic illustration of respective views of a mitral valve prosthesis, in accordance with some applications of the present invention.

Reference is now made to FIGS. 1A-D, which are schematic illustrations of respective views of a mitral valve prosthesis 100, in accordance with some applications of the present invention.

Mitral valve prosthesis 100 includes an inner support structure 102 and an outer support structure 104. Outer support structure 104 includes outer engagement arms (i.e., outer support arms) 106. As shown, mitral valve prosthesis 100 typically includes two outer engagement arms 106 to anatomically match the native mitral valve leaflets 107 (shown in FIG. 1B).

Sutured to inner support structure 102 is a prosthetic valve 118. For some applications, valve 118 is coupled to inner support structure 102, and/or to engagement arms 106 in accordance with techniques described in US 2008/0071368 to Tuval, which is incorporated herein by reference. Valve 118 can be formed of a biocompatible synthetic material, synthetic polymer, an autograft tissue, xenograft tissue, or other alternative materials. Valve 118 is a bi-leaflet bovine pericardium valve, a tri-leaflet valve, or any other suitable valve (e.g., a valve having a different number of leaflets).

Mitral-valve prosthesis 100 is typically placed at the subject's native mitral valve complex 128, as shown in FIG. 10. As used herein, including in the claims, the "native mitral valve complex" includes the native valve leaflets, the annulus of the valve, chordae tendineae, and papillary muscles. Inner support structure 102 and engagement arms 106 facilitate fixation of the mitral valve prosthesis with respect to native mitral valve complex 128, for example, due to the clamping of the native valve leaflets between the engagement arms and the inner support structure. Prosthetic valve 118 functions in a generally similar manner to a healthy native mitral valve, i.e., the prosthetic valve:

opens during diastole to permit the flow of blood from the subject's left atrium to the subject's left ventricle, and closes during systole to prevent the backflow of blood in the upstream direction from the subject's left ventricle to the subject's left atrium.

FIG. 10 shows prosthetic valve 118 in a closed state thereof (i.e., during systole). The prosthetic valve shown in FIG. 1C has three leaflets, although as described hereinabove, for some applications, valve 118 has a different number of leaflets.

Figure 1B:
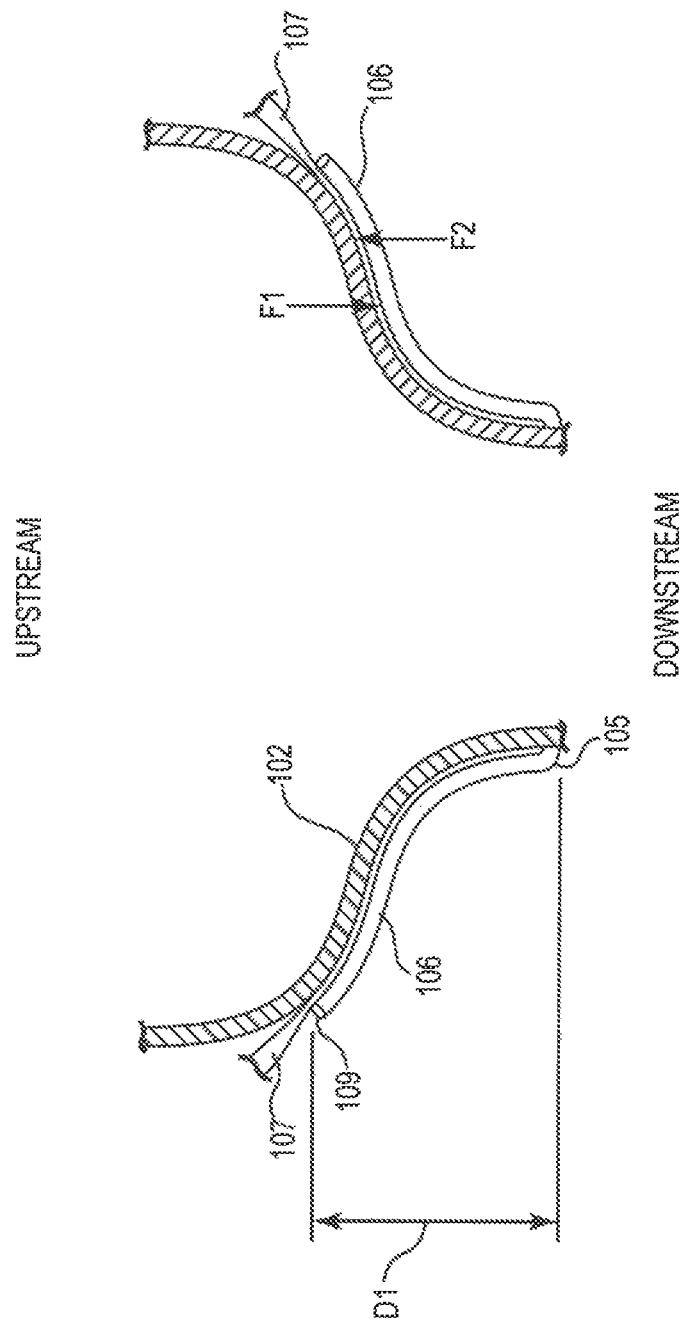
Figure 1C:
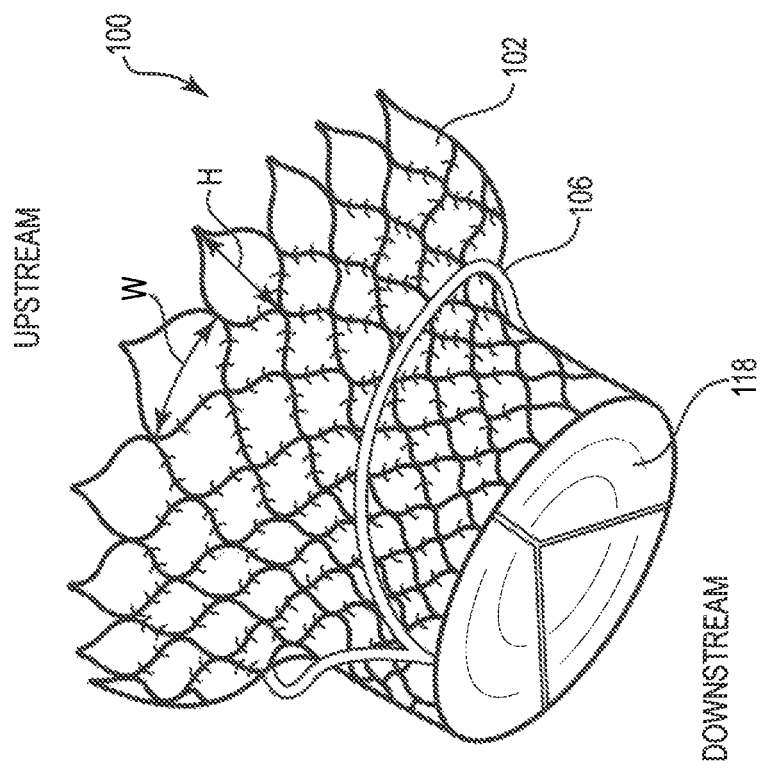
Figure 1D:
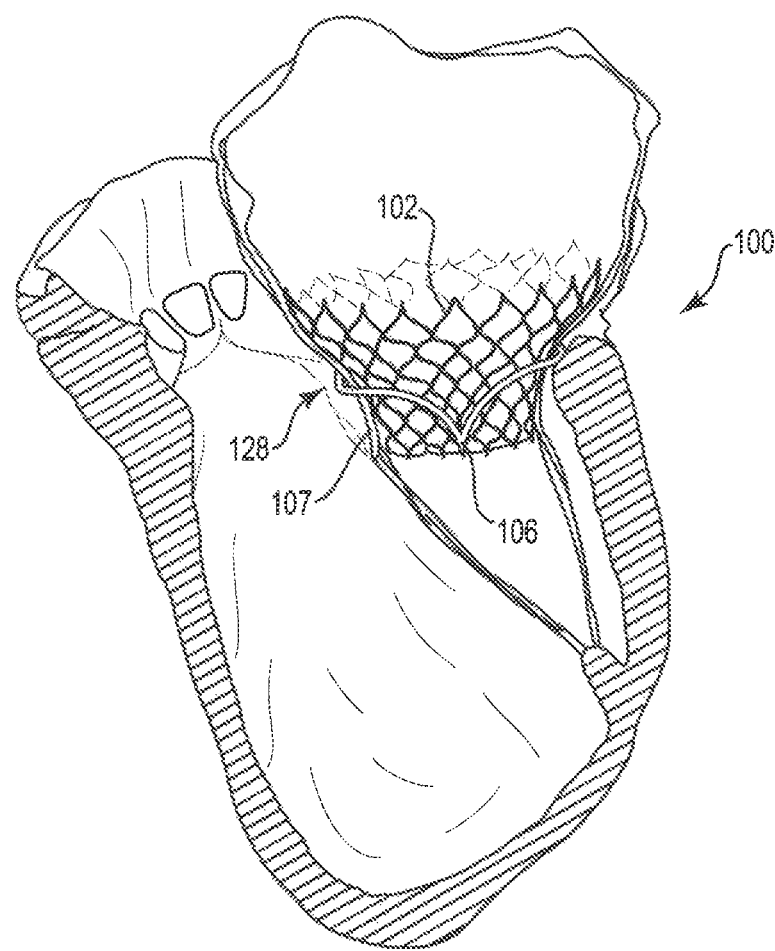
Figure 2A:
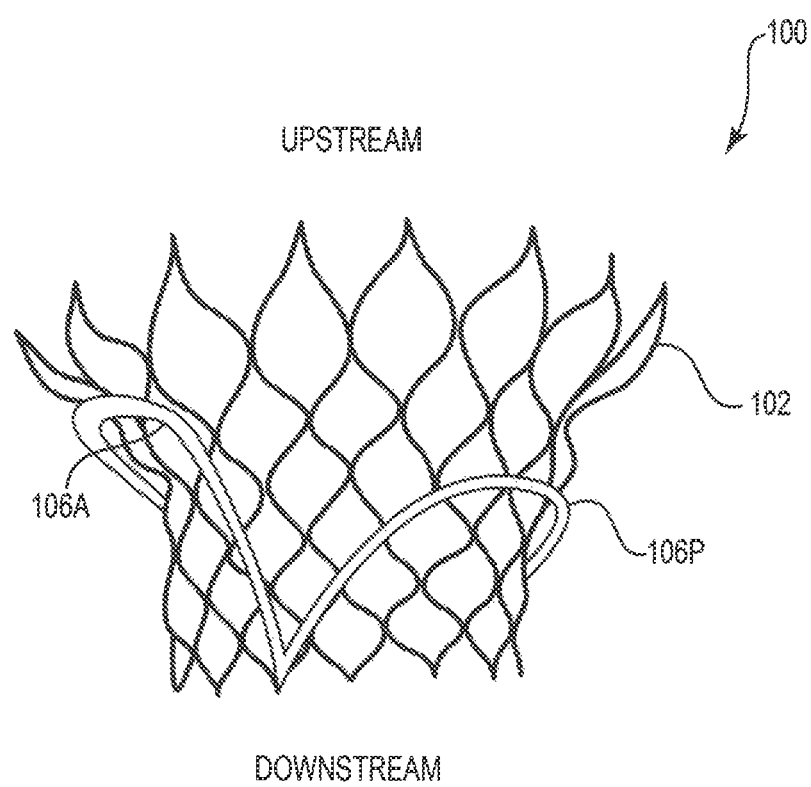
FIGS. 2A-D are schematic illustrations of respective views of a mitral valve prosthesis, in accordance with some applications of the present invention.
Figure 2B:
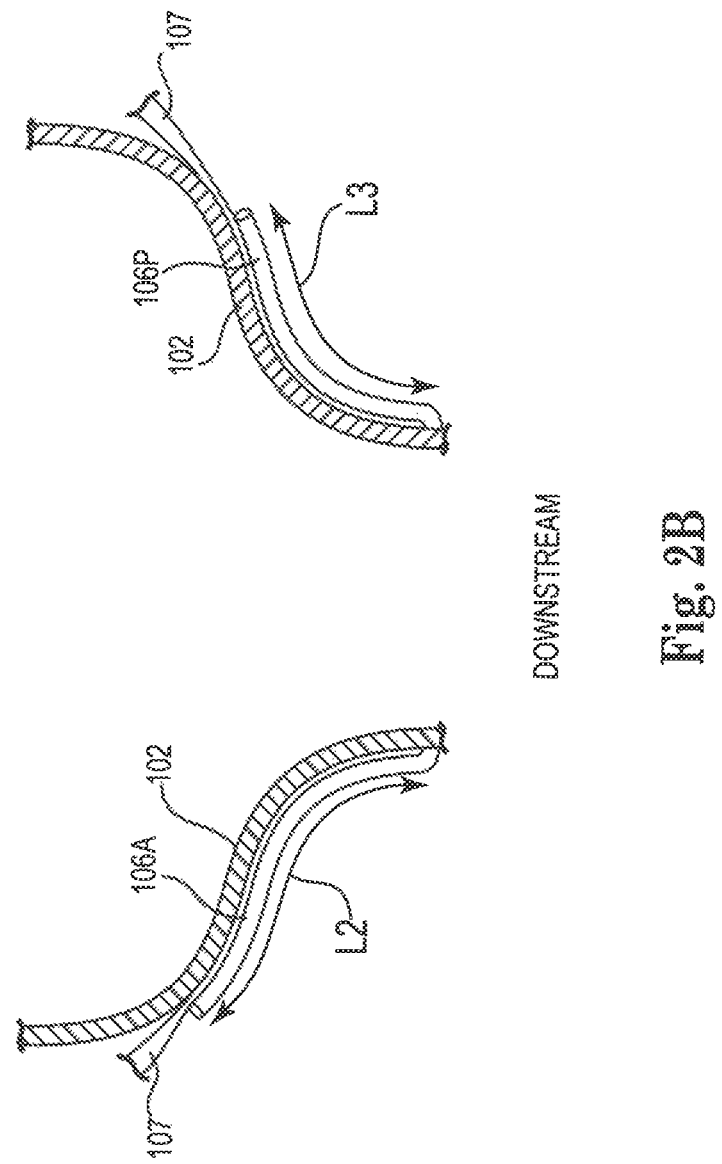
Figure 2C:
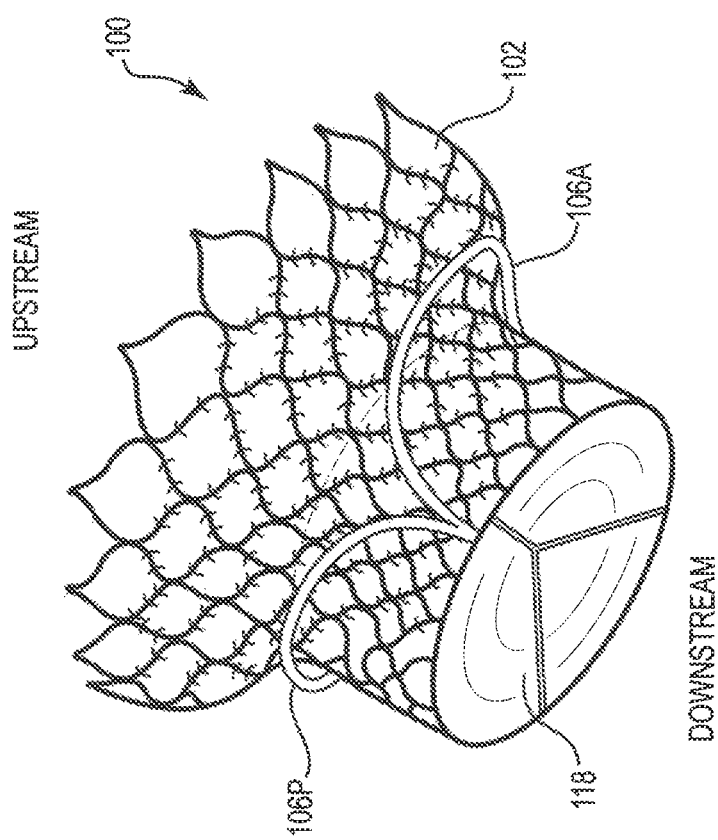
Figure 2D:
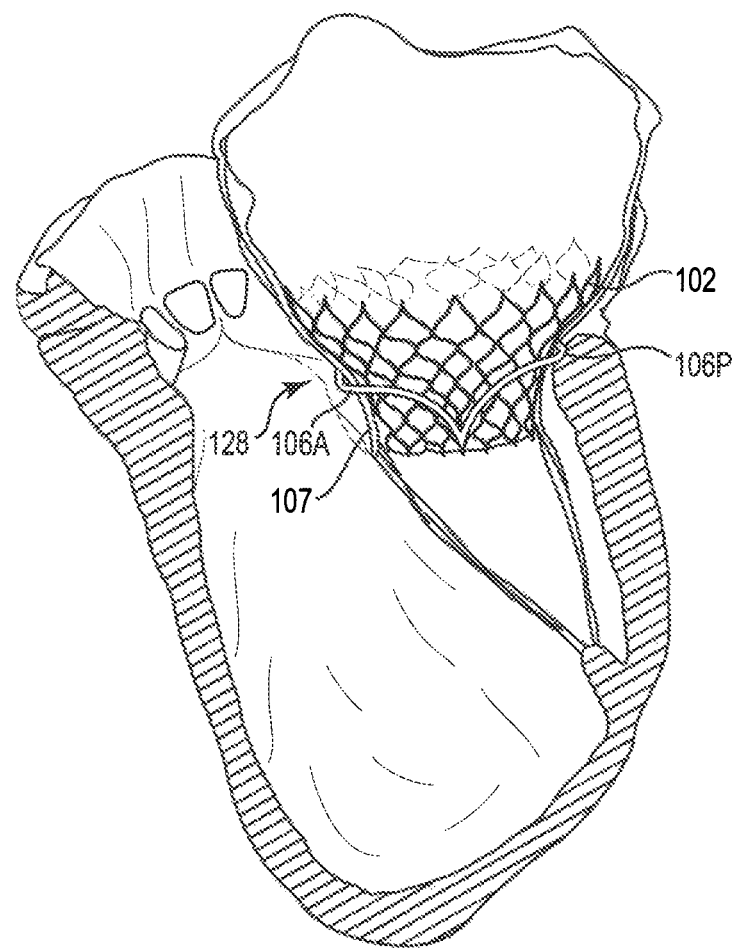

As shown in FIG. 1B, upon implantation, mitral valve prosthesis 100 is placed such that native mitral valve leaflets 107 are clamped between outer engagement arms 106 and inner support structure 102. The outer engagement arms typically immobilize leaflets of the native valve, by clamping the leaflets of the native valve.

Each outer engagement arm 106 is typically downwardly concave (i.e., concave in a downstream direction) at the region of the outer engagement arm that is adjacent to a downstream section 112 of inner support structure 102, when viewed from outside of the outer support structure, as shown in FIG. 1B, for example. The downstream ends of the engagement arms typically meet at commissure posts 108 (shown in FIG. 1A). For some applications, the engagement arms are coupled to the inner support structure at the commissure posts. Alternatively or additionally, the engagement arms, and/or the inner support structure is coupled to prosthetic valve 118 at the commissure posts, for example, in accordance with techniques described in US 2008/0071368 to Tuval, which is incorporated herein by reference. For some applications, mitral valve prosthesis 100 includes three engagement arms 106, three leaflets, and/or three commissure posts 108, or a different number of the aforementioned components.

Typically, engagement arms 106 facilitate the anchoring and/or orientation of the mitral valve prosthesis at the desired implantation site. In particular, the engagement arms prevent mitral valve prosthesis 100 from being dislodged upstream of native mitral valve complex 128 (e.g., when valve 118 is closed during systole and an upstream force is exerted on prosthesis 100). This is achieved, because, in response to upstream-directed blood flow pushing the valve prosthesis in the upstream direction (e.g., during systole), tissue of leaflets 107 of the native mitral valve complex exerts a downstream-directed force F1 (shown in FIG. 1B) on the engagement arms. For some applications (e.g., for the configuration of prosthesis 100 shown in FIGS. 4E-F), downstream ends of the native valve leaflets exert the downstream directed force on downstream portions of the engagements arms, i.e., at the portion of the engagement arms at which the engagement arms form shoulders with inner support structure 102. In addition, since the native leaflets are clamped between the engagement arms and inner support structure 102, the native leaflets anchor the prosthesis in place.

Typically, downstream ends 105 of engagement arms 106 are within 3 mm (e.g., within 1 mm) of downstream ends 119 of prosthetic leaflets 118 (see FIG. 1A), when measured in the direction of the longitudinal axis of the prosthesis. Further typically, upon implantation of the prosthesis, downstream ends 105 of engagement arms 106 are within 3 mm (e.g., within 1 mm) of downstream ends of the native valve leaflets 107 (see FIG. 1B). Thus, downstream ends of the engagement arms, downstream ends of the native valve leaflets, and downstream ends of the prosthetic valve leaflets are all typically within 3 mm (e.g., within 1 mm) of each other, when measured in the direction of the longitudinal axis of the prosthesis. Typically, this is achieved because (a) the prosthetic valve leaflets are coupled to the inner support structure such that downstream ends of the prosthetic valve leaflets are within 3 mm (e.g., within 3 mm) of the downstream ends of the engagement arms, and (b) longitudinal distance D1 (shown in FIG. 1B) from a downstream end 105 to an upstream end 109 of each of the engagement arms is less than 18 mm (e.g., less than 12 mm, or less than 10 mm), the longitudinal distance being measured in a direction of a longitudinal axis of the prosthesis. Further typically, the downstream ends of the engagement arms are coupled to the inner support structure within 3 mm (e.g., within 1 mm) of a downstream end of the inner support structure.

Inner support structure 102 includes a downstream section 112, and an upstream section 116. Inner support structure 102 is typically non-cylindrical. In accordance with respective applications, downstream section 112 of inner support structure 102 is formed in a straight fashion (i.e., cylindrical and parallel to the longitudinal axis of prosthesis 100), or in a flared fashion (i.e., diverging away from the longitudinal axis of prosthesis 100). Upstream section 116 of the inner support structure typically curves outwardly from the longitudinal axis of the prosthesis, such that the upstream section has a cross-sectional area that is greater than the cross-sectional area of downstream section 116. The upstream section of the inner support structure is typically wider than the native valve segment at the native annular level.

Typically, the non-cylindrical shape of the inner support structure facilitates the anchoring and/or orientation of the mitral valve prosthesis at the desired implantation site. In particular, the upstream section of the inner support structure being wider than the native valve segment at the native annular level prevents the mitral valve prosthesis from being dislodged downstream of native mitral valve complex 128. This is achieved, because in response to downstream-directed blood flow pushing the valve prosthesis in a downstream direction, tissue of native mitral valve complex 128 exerts an upstream-directed force F2 (shown in FIG. 1B) on the upstream section of the inner support structure. In addition, since the native leaflets are clamped between the engagement arms and inner support structure 102, the native leaflets anchor the prosthesis in place.

For some applications, the upstream section of the inner support structure being wider than the native valve segment at the native annular level improves sealing of prosthesis 100 against the atrial wall. For some applications, the inner support structure additionally exerts a radially-directed force on tissue of native mitral valve complex 128 that facilitates the anchoring and/or orientation of the prosthetic valve at the desired implantation site. For some applications, upstream section 116 of the inner support structure exerts the radially-directed force on tissue of native mitral valve complex 128.

Typically, when valve prosthesis 100 is implanted in native mitral valve complex 128, there are variations with time in the mechanical stress exerted on the inner support structure, caused by anatomical and pathological variations of surrounding structures. For some applications, relative to a more cylindrically-shaped inner support structure, non-cylindrical inner support structure resists changes in its shape due to mechanical stress that is exerted on the inner support structure. Typically, by resisting changes in its shape, the inner support structure facilitates the proper functioning of prosthetic valve 118.

Typically, inner support structure 102 is expandable (e.g., self-expandable). For example, the inner support structure may be formed of a memory alloy, such as nitinol, or another biocompatible metal. Similarly, outer support structure 104 may be formed of a memory alloy, such as nitinol, or another biocompatible metal. In accordance with respective applications, inner support structure 102 and outer support structure 104 are integrally formed, or comprise separate modular components that are attached to one another, as described in further detail hereinbelow.

For some applications, inner support structure 102 is designed to flex and deform in response to the natural cardiac movements of the heart through the cardiac cycle. Alternatively, inner support structure 102 is generally rigid, to avoid flexing or deformation during the cardiac cycle.

For some applications, inner support structure 102 includes one or more sections that are configured to expand to a restricted or preset diameter rather than expanding until restrained by surrounding anatomical structures. Thus, a portion of (or the entirety of) inner support structure 102 may have a predetermined configuration, irrespective of the surrounding anatomy. Typically, the predetermined configuration is such that the support structure expands so as to come into contact with the tissue of the native valve complex, but does not exert substantial pressure on the tissue of the native valve complex. For some applications, the controlled expansion diameter of the inner support structure improves the valve geometry, relative to a mitral valve prosthesis having an inner support structure that expands until restrained by the surrounding anatomy. Typically, at least a portion of inner support structure 102 (and further typically, all of the inner support structure) expands until restrained by the surrounding anatomy.

As shown (in FIGS. 1A, 1C and 1D, for example), for some applications, downstream section 112 and upstream section 116 of inner support structure 102 include generally-diamond-shaped cells 103, which are described in further detail hereinbelow, with reference to FIG. 3. Alternatively, other shapes and configurations of the cells 103 are employed, for example, as described hereinbelow. For some applications, the locations of junctions of members of a cell with those of adjacent cells are positioned asymmetrically, and/or cells are shaped asymmetrically. For some applications, structural members of the cells are shaped curvilinearly. Alternatively, structural members of the cells are formed in a generally zigzag configuration to form symmetrical or asymmetrical cells. For some applications, using structural members that are shaped in a zigzag configuration distributes the stress associated with radial expansion and contraction of the support member to a plurality of points between junctions. In accordance with respective applications, the inner support structure includes heterogeneous patterns of cells, or homogeneous patterns, or both.

Typically, the ratio of the cell height (H) to cell width (W) (H and W shown in FIGS. 1A and 1C) of cells 103 is greater than 0.5:1 and/or less than 3:1, e.g., 0.5:1 to 3:1. For example, the ratio may be greater than 1.5:1 and/or less than 2.5:1, e.g. 1.5:1 to 2.5:1. For example, the ratio may be greater than 1.75:1 and/or less than 2.25:1, e.g., 1.75:1 to 2.25:1. For some applications, having cells having the aforementioned ratios of cell height to cell width facilitates the expansion and/or the maintenance of the structure of inner support structure 102.

Reference is now made to FIGS. 2A-D, which are schematic illustrations of respective views of mitral valve prosthesis 100, in accordance with some applications of the present invention. For some applications, a length L2 (shown in FIG. 2B) of an anterior engagement arm 106A is greater than a length L3 of a posterior engagement arm 106P. For some applications, the different lengths of the anterior and posterior engagement arms correspond to the anatomy of most people, most people having a native anterior mitral valve leaflet having a greater length than their native posterior mitral valve leaflet. In all other aspects, the mitral valve prosthesis shown in FIGS. 2A-D is generally similar to the mitral valve prosthesis described with reference to FIGS. 1A-D.

Typically, length L2 of the anterior engagement arm is greater than 2 mm and less than 35 mm, e.g., 15 mm to 25 mm. Further typically, length L3 of the posterior engagement arm is greater than 2 mm and less than 35 mm, e.g., 7 mm to 23 mm. Still further typically, for applications in which the anterior and posterior engagement arms have different lengths, the ratio of the length of the anterior engagement arm to the length of the posterior engagement arm is greater than 1.1:1, and/or less than 15:1, e.g., 1.3:1 to 2:1.

Figure 3:
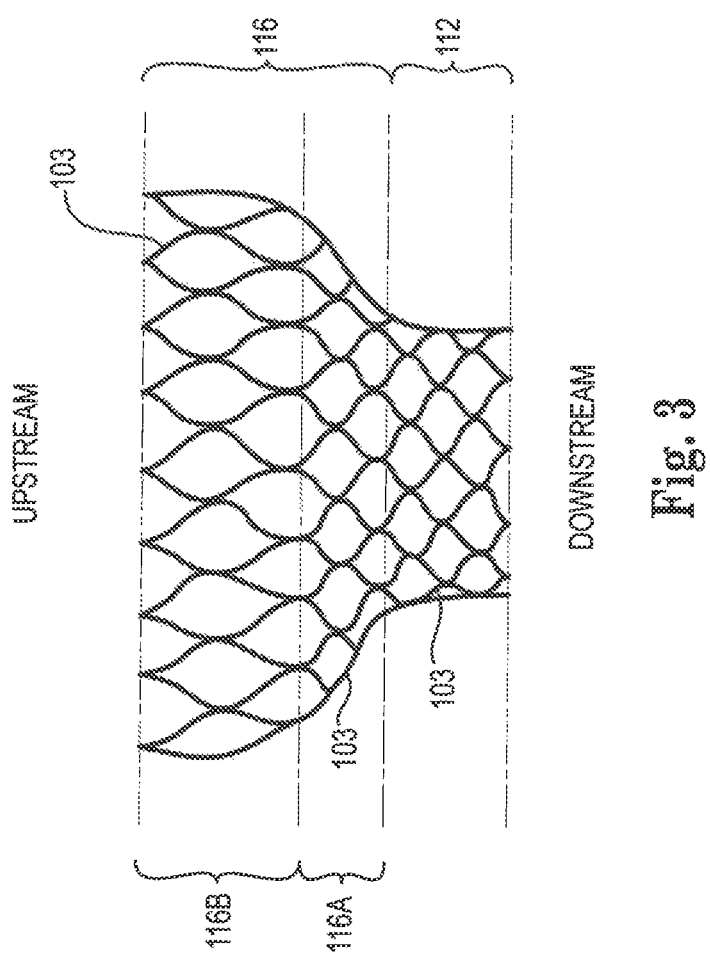
FIG. 3 is a schematic illustration of an inner expandable support structure of the prosthesis, in accordance with some applications of the present invention.

Reference is now made to FIG. 3, which is a schematic illustration of inner support structure 102 of mitral valve prosthesis 100, in accordance with some applications of the present invention. As shown in FIG. 3, for some applications, cells 103 of the inner support structure have respective characteristics at different longitudinal locations along the inner support structure.

For some applications, downstream section 112 of the inner support structure includes cells that have relatively short heights, and relatively high strut width relative to height. In addition, the cells typically define relatively high angles. For some applications, cells having the aforementioned characteristics provide the downstream section of the support structure with a high radial force area to maintain circularity of the valve, and/or fatigue resistance against high pressure gradients. Typically, the downstream section of the support structure is relatively short, so as to minimize protrusion of the inner support structure into the ventricle beyond the annular plane.

For some applications, upstream section 116 of inner support structure includes an intermediate section 116A, and an upstream-most section 116B, intermediate section 116B being disposed between upstream-most section 116A and downstream section 112 of the support structure. The cells of intermediate section 116A and upstream-most section 116B have respective characteristics.

Cells 103 of intermediate section 116A typically have relatively short heights, and relatively high strut width relative to height. In addition, the cells typically define relatively high angles. For some applications, cells having the aforementioned characteristics provide the intermediate section of the support structure with high pinching resistance. The intermediate section of the support structure is typically shaped so as to facilitate annular sealing on the atrial side of the mitral valve complex, above the annulus. Alternatively or additionally, the intermediate section of the support structure is shaped so as to prevent downstream migration of mitral valve prosthesis 100.

Cells 103 of upstream-most section 116B typically have large heights. The shape of the cells of the upstream-most portion typically exert relatively low radial pressure on the surrounding anatomy, such that the upstream-most section of the support structure enhances sealing of the native valve complex, by conforming to the atrial anatomy. Furthermore, by conforming to the atrial anatomy, the upstream-most section preserves atrial contraction. The upstream-most section of the support structure typically has a relatively large cross-sectional area, which typically prevents downstream migration of mitral valve prosthesis 100.

Reference is now made to FIGS. 4A-F, which are schematic illustrations of mitral prosthesis 100, in accordance with some applications of the present invention. As shown in FIGS. 4A-D, for some applications, inner support structure 102 of mitral valve prosthesis 100 does not extend to the downstream end of the prosthesis. For example, as shown, the inner support structure may extend from an upstream end 120 to substantially halfway between upstream and downstream ends of the prosthesis, such that the downstream end of the inner support structure is between 2 mm and 15 mm from downstream ends 119 of prosthetic leaflets 118. Alternatively, inner support structure 102 of mitral valve prosthesis 100 does extend substantially to the downstream end of the prosthesis, for example, such that the downstream end of the inner support structure is within 1 mm of downstream ends 119 of prosthetic leaflets 118 (a shown in FIG. 1C, for example).

Figure 4B:
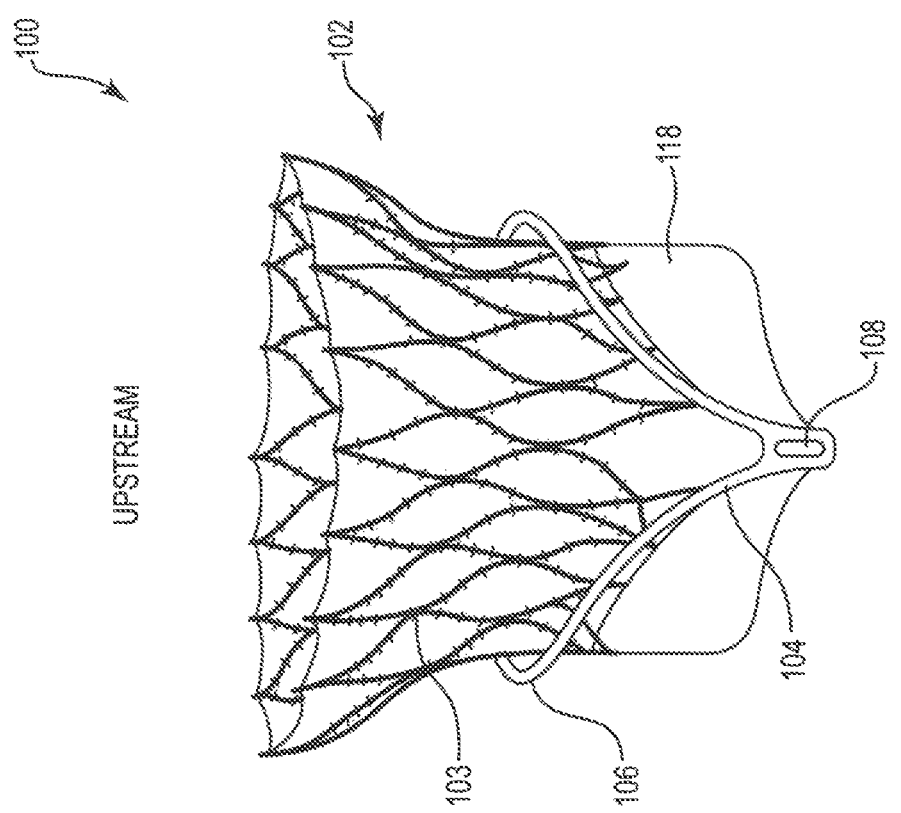
Figure 4D:
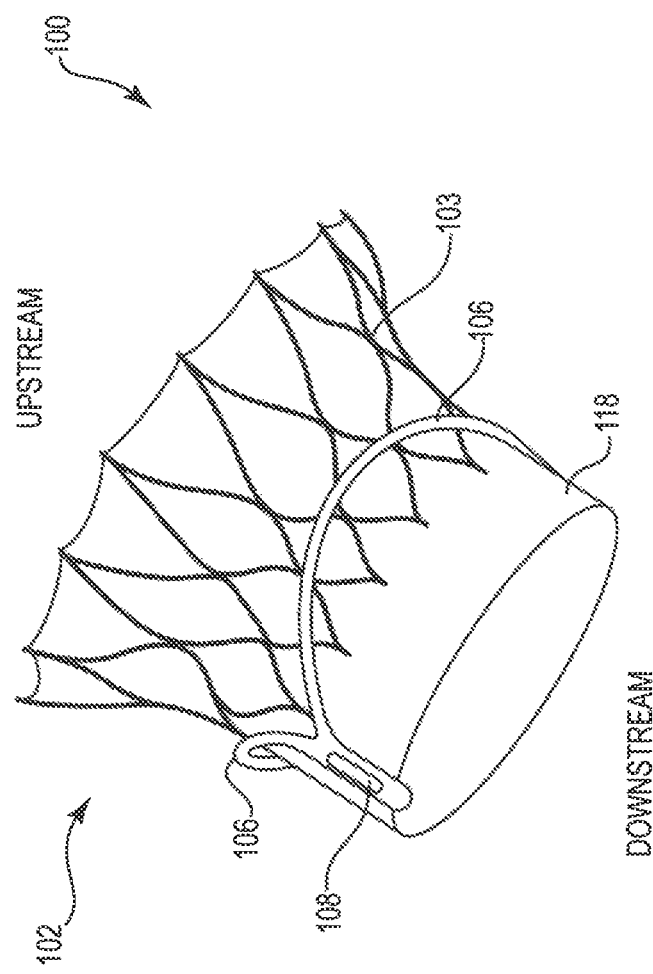

For some applications, outer support structure 104 includes outer engagement arms 106 that are coupled to upstream ends of commissure post 108, rather than being coupled to downstream ends of the commissure posts, as described with reference to FIGS. 1A-D. As shown in FIG. 4B, for some applications, commissure post 108 extends downstream from the ends of engagement arms 106. For such applications, the downstream ends of commissure posts 108 are level with the ends of prosthetic valve leaflets 118. In all other respects, prosthesis 100 of FIG. 4B is generally similar to prosthesis 100 as described hereinabove with reference to FIGS. 1-3.

For some applications, not having the inner support structure extend to the downstream end of the prosthesis, allows for prosthesis 200 to be constructed of less material, and/or reduces the weight of prosthesis 200.

Figure 4F:
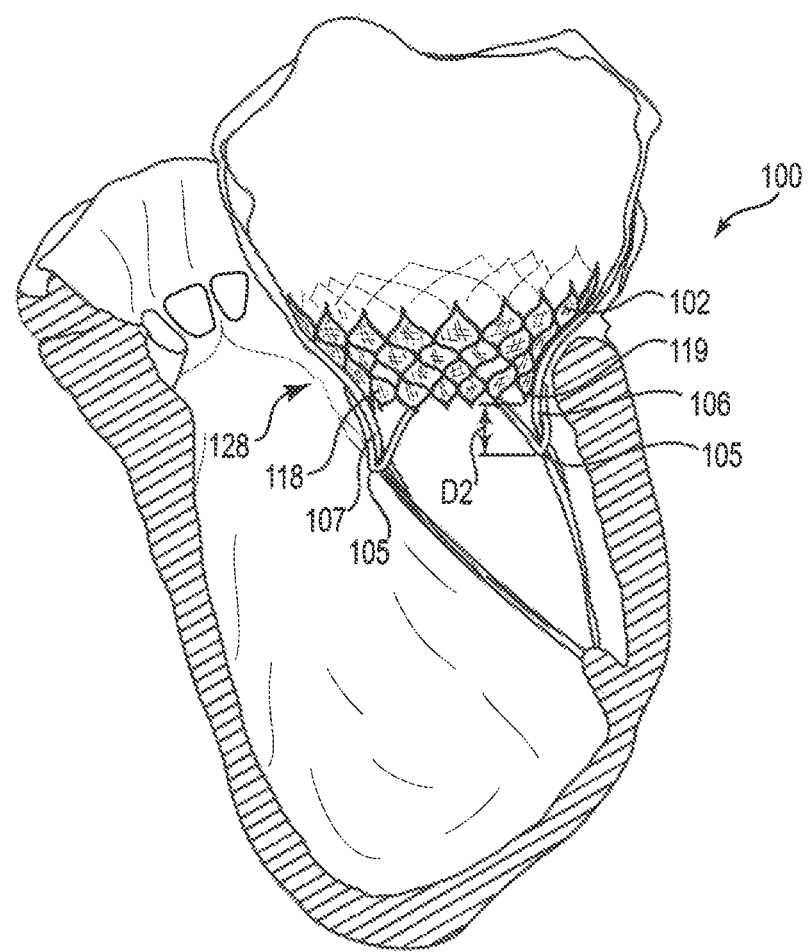

As shown in FIGS. 4E-F, for some applications, engagement arms 106 and prosthetic valve 118 are coupled to inner support structure 102 such that downstream ends 119 of the prosthetic valve leaflets are at a longitudinal distance D2 upstream of the downstream ends 105 of the engagement arms. Thus, prosthesis 100 is configured such that upon implantation thereof, the downstream end of the inner support structure 102 and downstream ends 119 of the prosthetic valve leaflets 118 are at a longitudinal distance D2 upstream of the downstream ends of the native valve leaflets 107. Typically, distance D2 is at least 4 mm, e.g., at least 10 mm. Further typically, upon implantation of the prosthesis, downstream ends of native valve leaflets of the native mitral valve complex, and downstream ends 105 of the engagement arms are disposed at a longitudinal distance from one another of less than 3 mm.

Figure 5A:
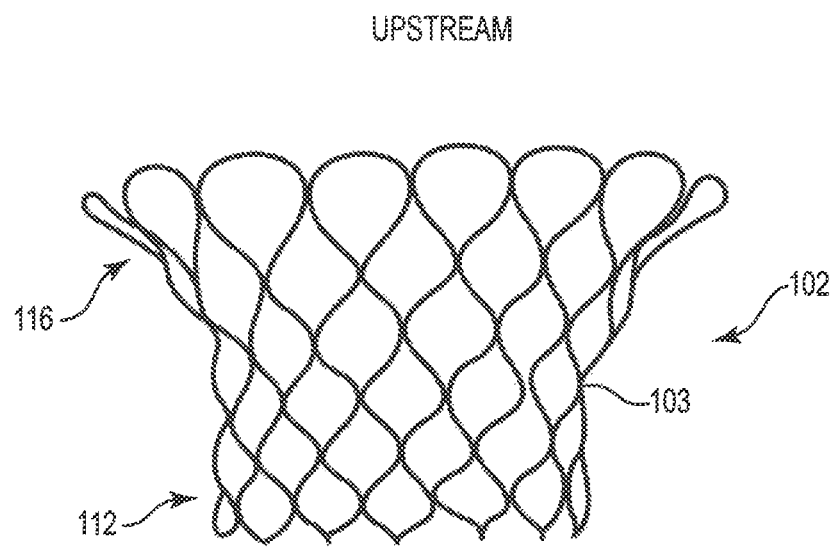
FIGS. 5A-B are schematic illustrations of the inner expandable support structure of the prosthesis, in accordance with some applications of the present invention.
Figure 5B:
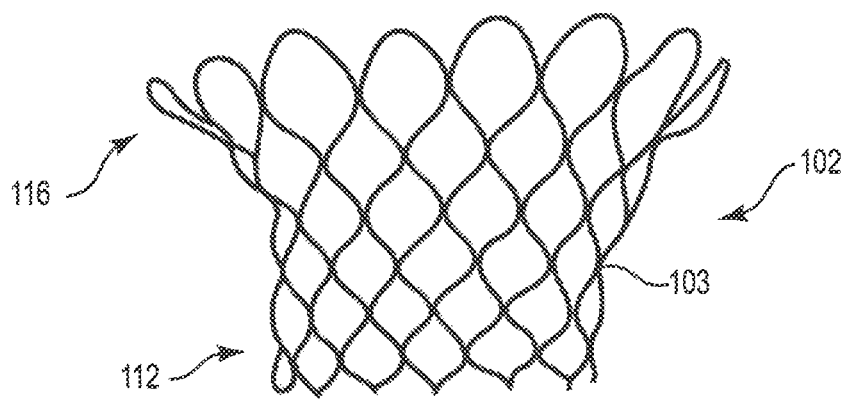

Reference is now made to FIGS. 5A-B, which are schematic illustrations of inner expandable support structure 104 of mitral valve prosthesis 100, in accordance with some applications of the present invention. As shown, for some applications, apices of the inner support structure at the upstream end of the support structure are rounded. FIG. 5B shows slightly rounded apices, and FIG. 5A shows more rounded apices. For some applications, using apices that are rounded reduces trauma to the atrial endocardium, and/or enhances local radial stiffness of the inner support structure, relative to using an inner support structure having a non-rounded upstream end. For some applications, the downstream end of the inner support structure also has rounded cell-apices. In alternative applications, the apices of the cells at the downstream end of the inner support structure are non-rounded (as shown in FIGS. 5A-B), or the apices of the cells at both ends of the inner support structure are non-rounded (as shown in FIG. 1A).

Reference is now made to FIGS. 6A-D, which are schematic illustrations of inner expandable support structure 102 of prosthesis 100, in accordance with some applications of the present invention.

Figure 6A:
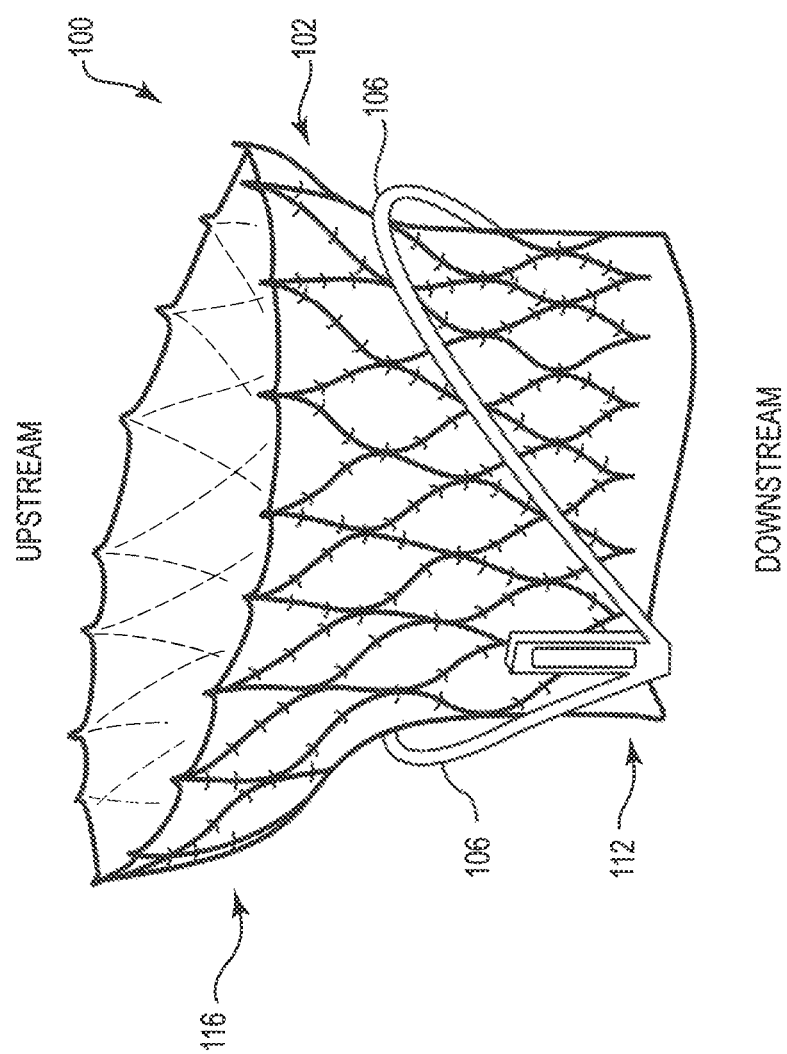
FIGS. 6A-D are schematic illustrations of the inner expandable support structure of the prosthesis, in accordance with some applications of the present invention.
Figure 6B:
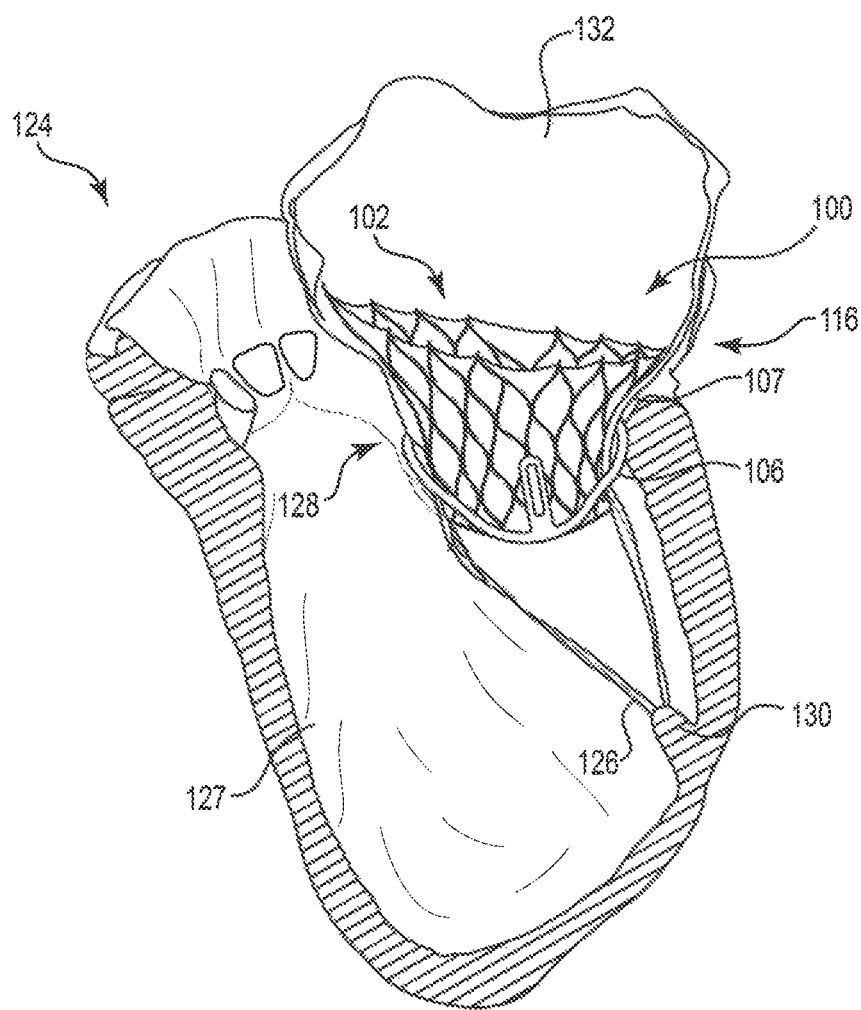

Prosthesis 100 shown in FIGS. 6A-B is generally similar to the prosthesis described hereinabove, the prosthesis including inner support structure 102 and outer support structure 104. However, the shape of inner support structure 102 differs from the shape of inner support structure 102 of FIG. 1A. Specifically, upstream section 116 of inner support structure 102 is formed asymmetrically to accommodate the anterior horn of the atrium (which is associated anatomically with the position of the aortic valve), as shown in FIG. 6B, which shows the prosthesis implanted inside the subject's heart. For example, as shown in FIG. 6A, the length of prosthesis 100 from downstream section 112 to upstream section 116 is increased at an area corresponding to the anterior horn of the atrium. This area also extends radially farther from the longitudinal axis of the prosthesis, in order to accommodate the anterior horn. As described hereinabove, upstream section 116 is generally wider than the native valve segment at the native annular level. Such a configuration prevents migration of prosthesis 100 into the ventricle and improves sealing of prosthesis 100 against the atrial wall.

For some applications, as shown, downstream section 112 of the inner support structure has a circular cross-section, while upstream section 116 has a non-circular cross-section. Typically, for applications in which inner support structure is shaped to accommodate the anterior horn of the atrium, the cross-section of inner support structure 102 is a non-uniform, non-circular shape, for example, a D-shape, or oval.

FIG. 6B is a sagittal cut through a human heart 124 depicting the implanted mitral valve prosthesis 100 of FIG. 6A. Chordae tendineae 126, which are disposed in left ventricle 127, connect native mitral valve 128 to papillary muscles 130. Engagement arms 106 wrap around leaflets 107 of native mitral valve 128. As shown in FIG. 6B, upstream section 116 has a non-circular, asymmetric shape to accommodate the anterior horn of atrium 132, which is associated anatomically with the position of aortic valve 134. The shape of upstream section 116 facilitates axial fixation, facilitates prevention of outflow obstruction, and/or facilitates sealing of prosthesis 100 against the wall of left atrium 132.

Figure 6C:
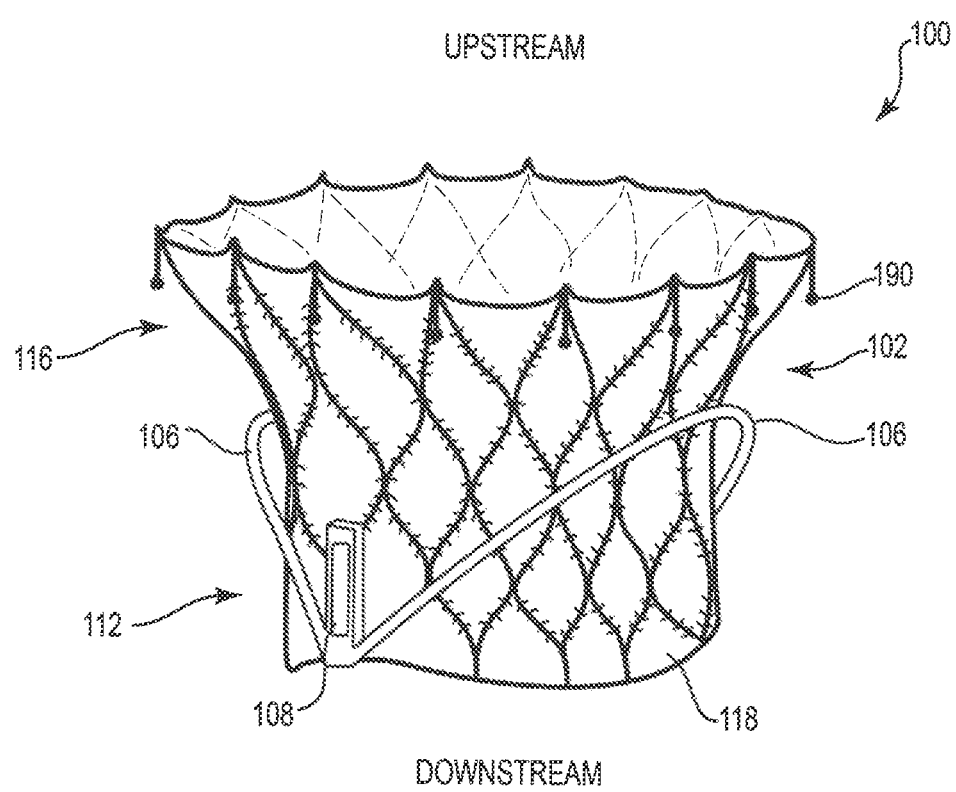
Figure 6D:
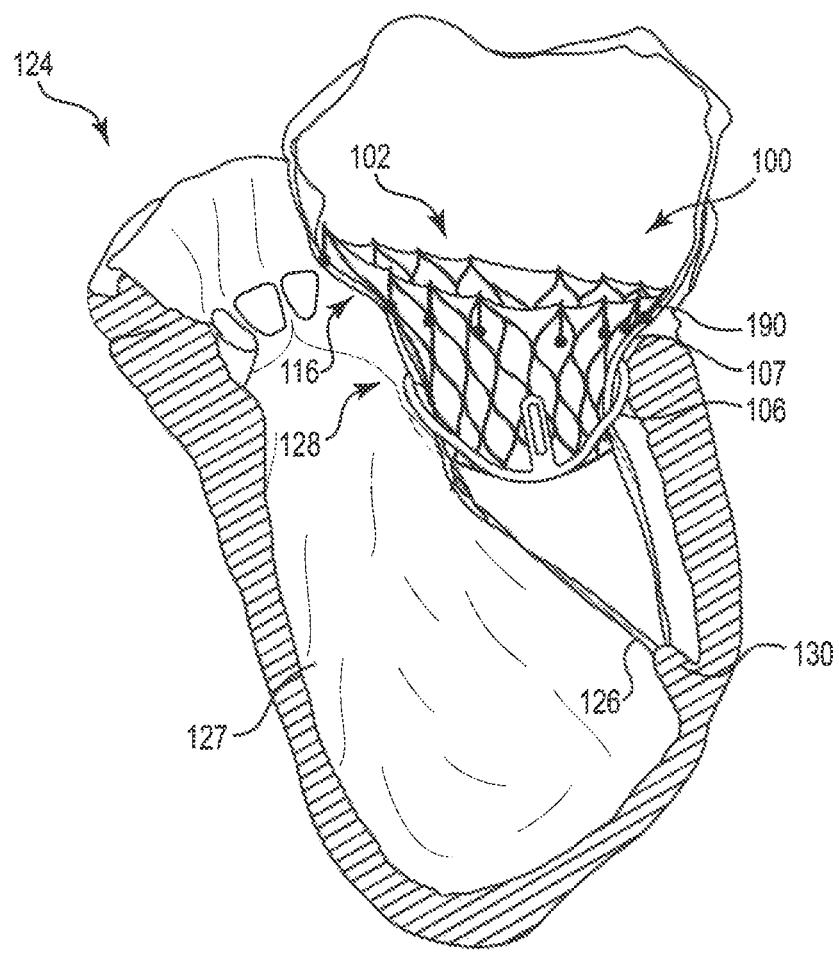

Prosthesis 100 shown in FIGS. 6C-D is generally similar to the prosthesis described hereinabove, the prosthesis including inner support structure 102 and outer support structure 104. However, in accordance with some applications of the invention, upstream section 116 of the inner support structure includes fixation members 190 (e.g., barbs, as shown, hooks, anchors, or clips) to provide further fixation support and to prevent migration of prosthesis 100 into the ventricle.

FIG. 6D is a sagittal cut through a human heart 124, depicting an implanted mitral valve prosthesis 100. As shown in FIG. 6D, upstream section 116 has a non-circular, asymmetric shape to accommodate the anterior horn of left atrium 132. The shape of upstream section 116 facilitates axial fixation, facilitates prevention of outflow obstruction, and/or facilitates sealing of prosthesis 100 against the wall of left atrium 132. Further, barbs 190 penetrate to the mitral annulus and serve as a locking mechanism to prevent migration of prosthesis 100 into left ventricle 127.

Reference is now made to FIGS. 7A-F, which are schematic illustrations of respective steps of a transapical implantation procedure of mitral valve prosthesis 100 (described hereinabove with reference to any of FIGS. 1-6), in accordance with some applications of the present invention.

Figure 7A:
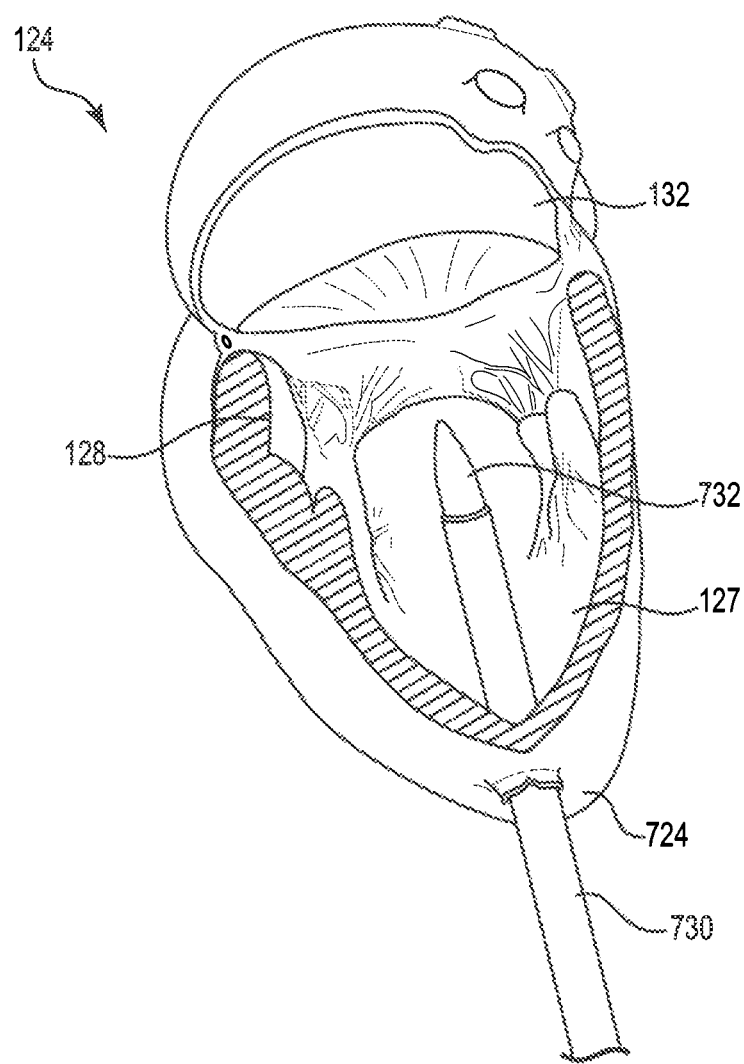
FIGS. 7A-F are schematic illustrations of respective steps of a transapical implantation procedure of the mitral valve prosthesis, in accordance with some applications of the present invention.
Figure 7B:
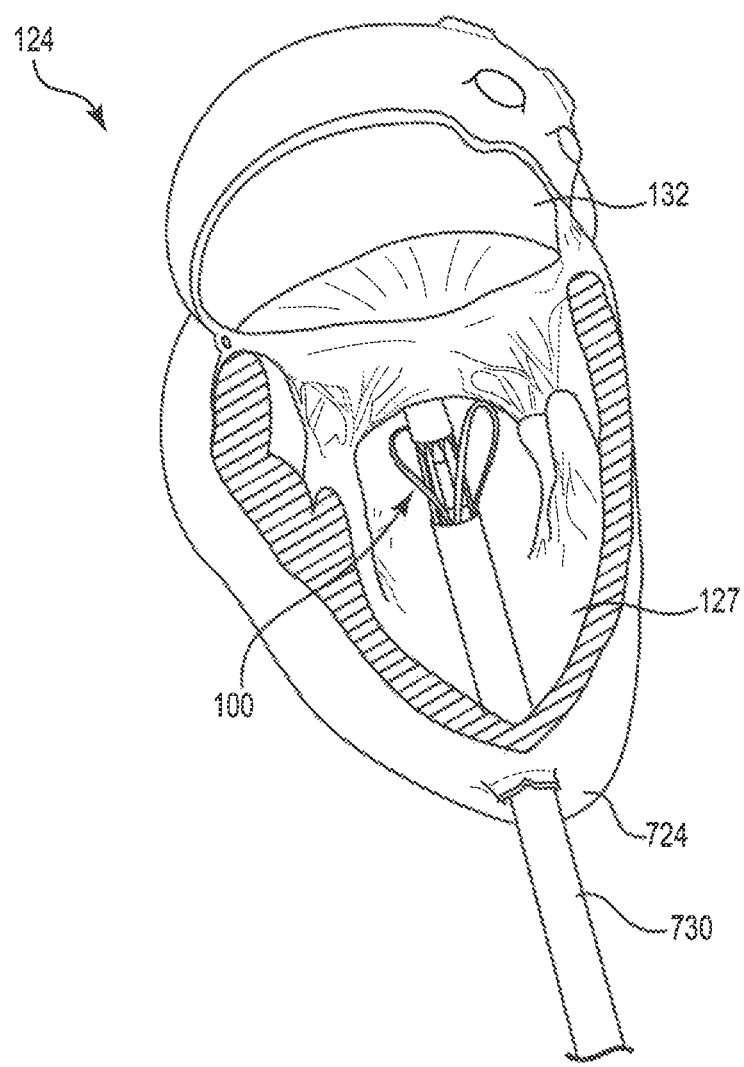

As shown in FIG. 7A, a trocar (i.e., an overtube) 730 is inserted into the left ventricle 127 through an incision created in the apex 724 of a patient's heart 124. A dilator 732 is used to aid in the insertion of trocar 730. In this transapical approach, the native mitral valve 128 is approached from the downstream direction. As shown in FIG. 7B, subsequently, trocar 730 is retracted sufficiently to release the self-expanding engagement arms 106 of the mitral valve prosthesis. Typically, dilator 732 is presented between leaflets of valve 128. Trocar 730 can be rotated and adjusted as necessary to align the valve prosthesis so that engagement arms 106 are positioned so as to be placed around leaflets of native valve 128.

Figure 7C:
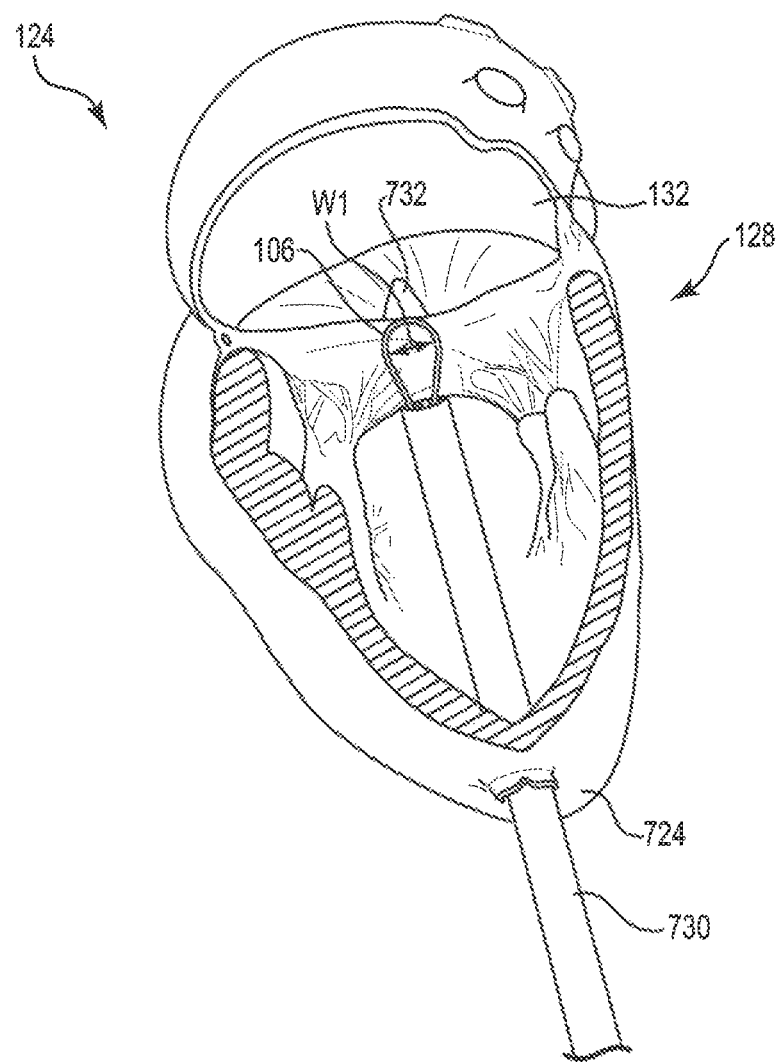
Figure 7D:
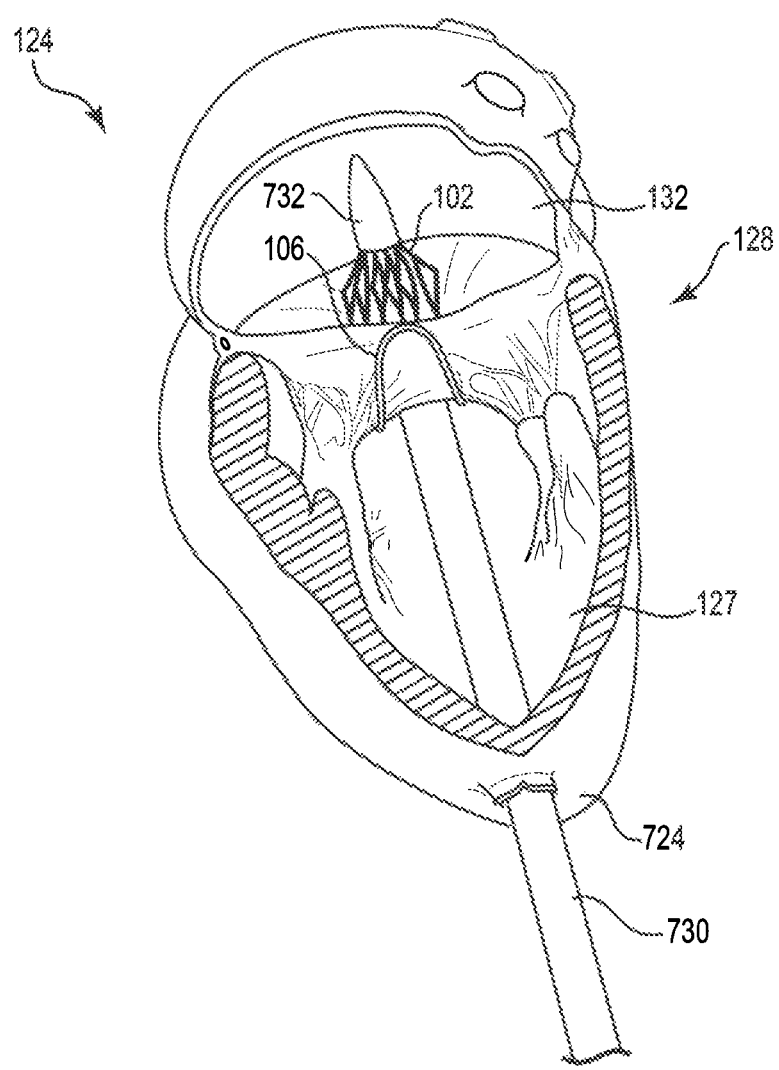
Figure 7E:
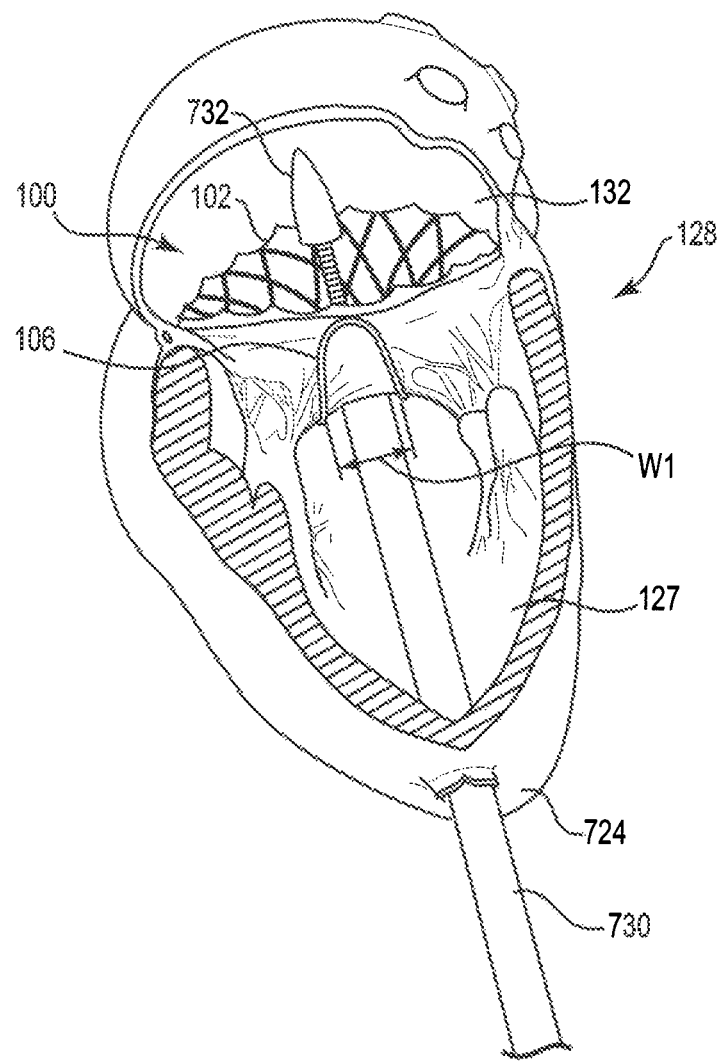
Figure 7F:
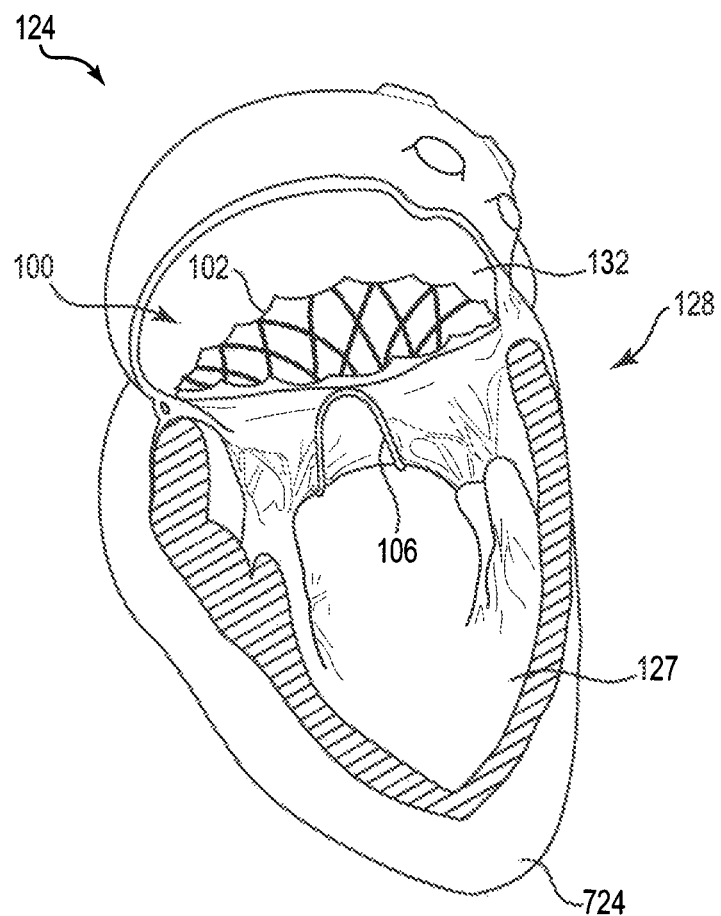

As shown in FIG. 7C, subsequently, trocar 730 and the valve prosthesis are advanced forward, such that outer engagement arms 106 are placed upon leaflets of native valve 128. As shown in FIG. 7D, subsequently, dilator 732 is advanced into the left atrium to further expose inner support structure 102, and more specifically, to begin disengaging upstream section 116 from dilator 732. FIG. 7E shows upstream section 116 released from dilator 732, and expanded to press against the interior wall of native mitral valve 128. The expansion of the upstream section is typically such that the native valve leaflets are clamped between the inner support structure and the engagement arms. (For some applications, upstream section 116 does not expand against the interior wall of the native valve so as to exert a substantial radial force on the inner wall of the valve. Rather, the upstream section is configured to clamp the native valve leaflets against the engagement arms by exerting a downstream-directed axial force against the leaflets.) Subsequently, trocar 730 is withdrawn from heart 124, and the incision in apex 724 is closed, as shown in FIG. 7F.

It is noted that in the transition from FIG. 7C to FIG. 7E, the width W1 that is spanned by each of the engagement arms increases. Typically, during placement of the engagement arms on the native valve leaflets, each of the engagement arms spans a width that is less than 12 mm, e.g. less than 8 mm, as shown in FIG. 7C. Typically, this prevents the engagement arms from coming into contact with the papillary muscles, since the engagement arms span a sufficiently narrow width so as to be placed between the papillary muscles. Further typically, this allows the native valve to continue functioning at least in part, since there are portions of the leaflets that are outside the engagement arms that may continue to open and close, at least partially. Subsequently, the engagement arms expand (typically, due to the expansion of the inner support structure) such that each of the engagement arms spans a width of more than 15 mm, e.g., more than 35 mm, as shown in FIG. 7E.

Reference is now made to FIGS. 8A-F, which are schematic illustrations of respective steps of a transatrial implantation procedure of mitral valve prosthesis 100 (described hereinabove with reference to any of FIGS. 1-6), in accordance with some applications of the present invention.

Figure 8A:
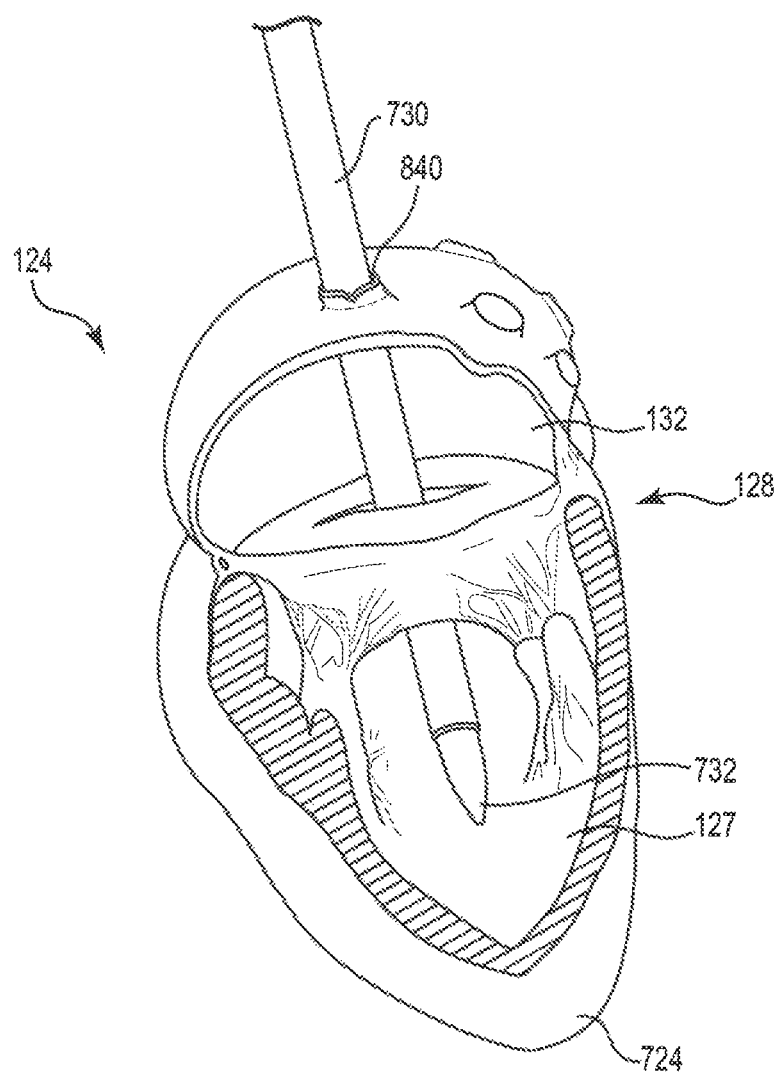
FIGS. 8A-F are schematic illustrations of respective steps of a transatrial implantation procedure of the mitral valve prosthesis, in accordance with some applications of the present invention.
Figure 8B:
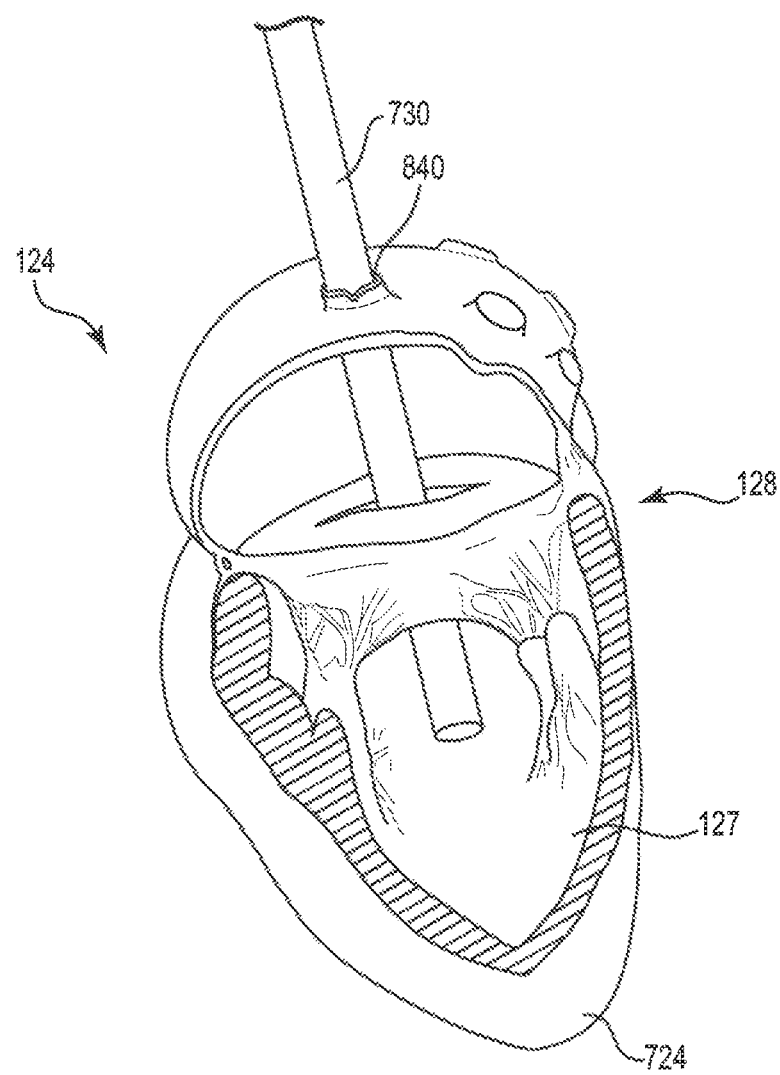
Figure 8C:
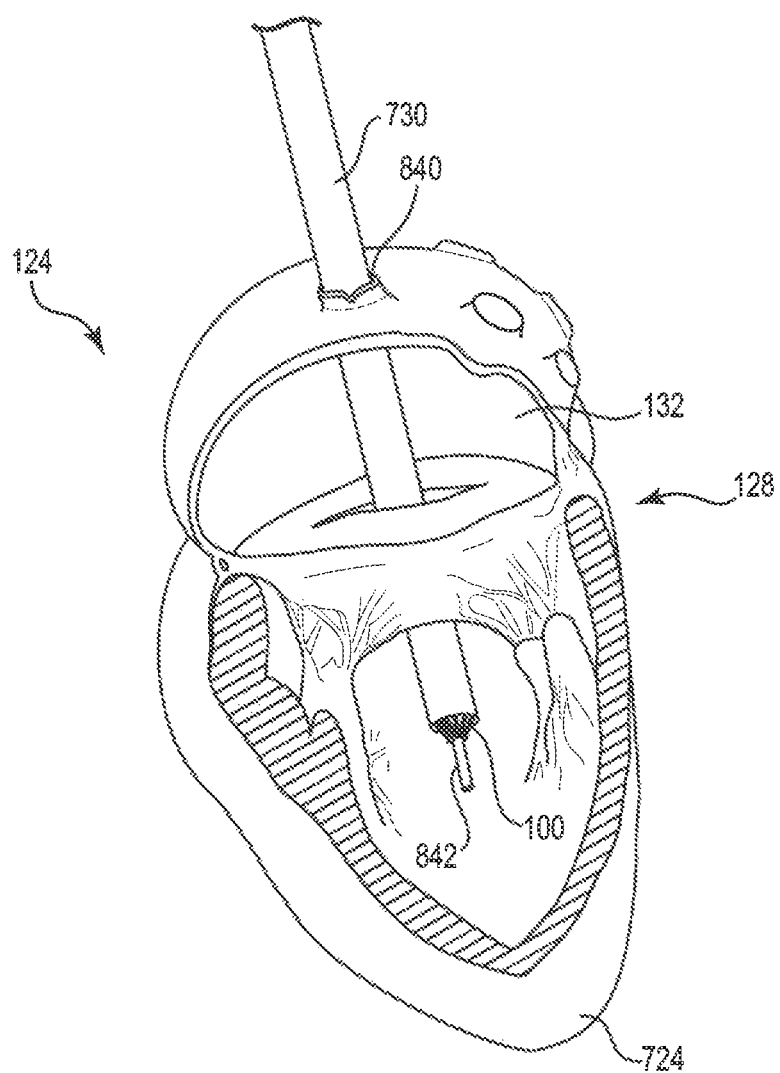
Figure 8D:
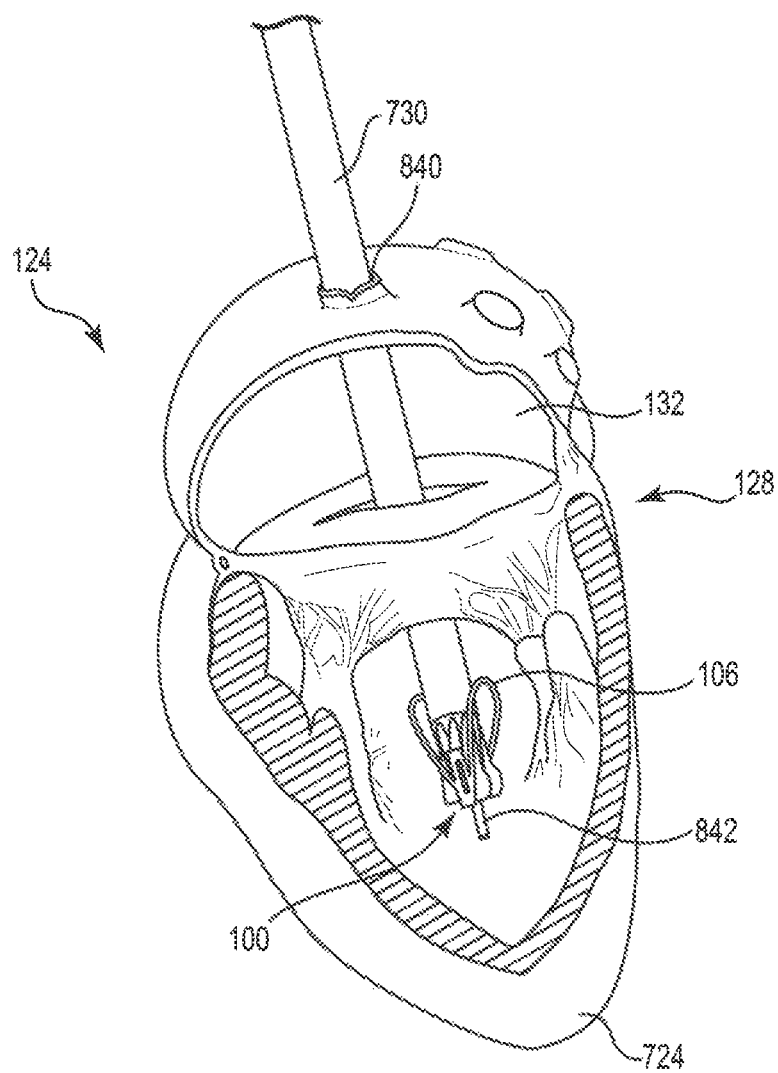
Figure 8E:
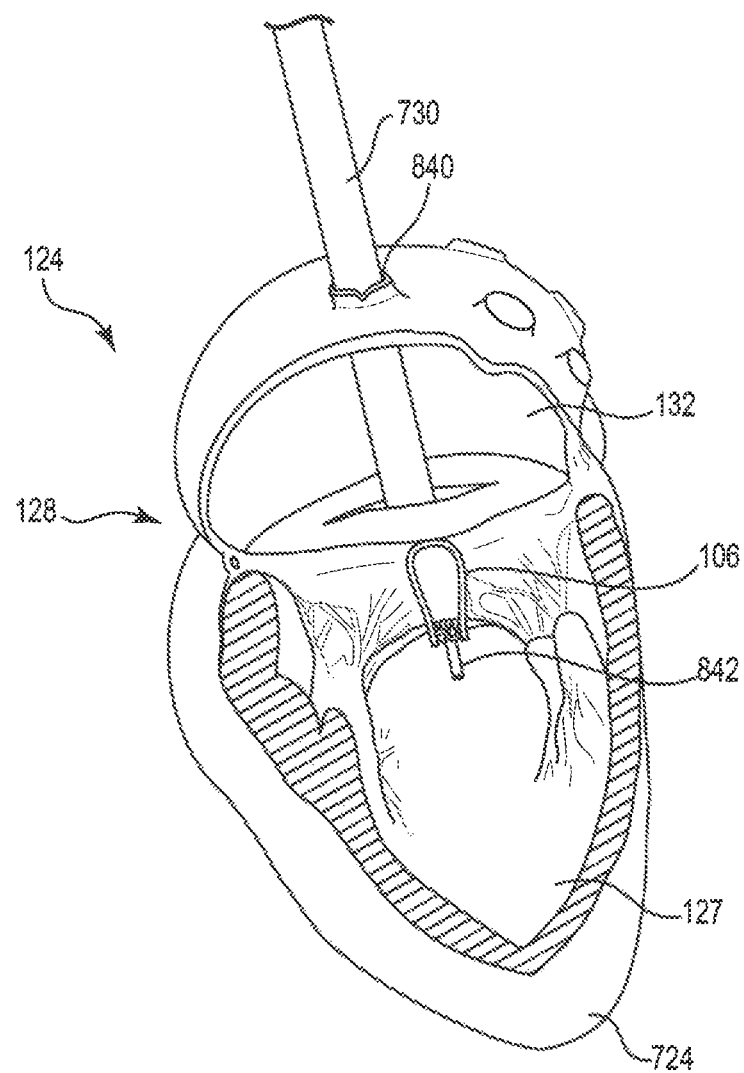
Figure 8F:
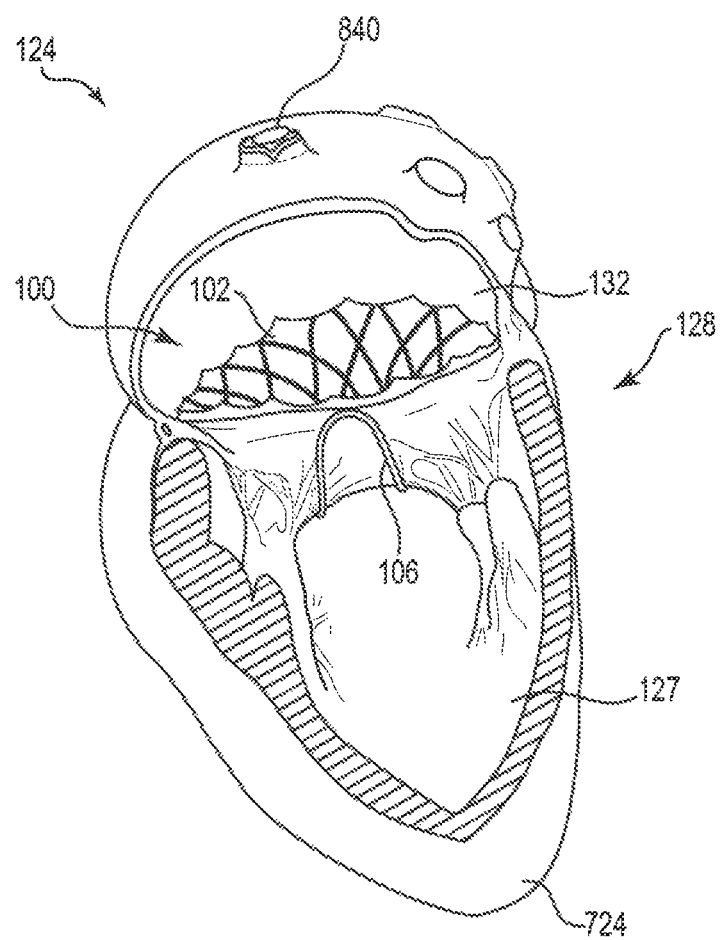

As shown in FIG. 8A, dilator 732 and trocar 730 are inserted through an incision 840 made in the wall of the left atrium of heart 124. Dilator 732 and trocar 730 are advanced through the native mitral valve 128 and into the left ventricle of heart 124. As shown in FIG. 8B, subsequently, dilator 732 is withdrawn from trocar 732. Subsequently, a guide wire 842 is advanced through trocar 730 to the point where mitral valve prosthesis 100 comes to the end of trocar 730, as shown in FIG. 8C. As shown in FIG. 8D, subsequently, mitral valve prosthesis 100 is advanced sufficiently to release the self-expanding engagement arms 106 from trocar 730. Trocar 730 is typically rotated and adjusted as necessary to properly align the valve prosthesis with native valve 128. Subsequently, trocar 730 is withdrawn slightly so as to place engagement arms 106 around the outside of leaflets of native valve 128, as shown in FIG. 8E. Subsequently, trocar 730 is completely withdrawn from heart 124 such that mitral valve prosthesis 100 self-expands into position and assumes the function of native mitral valve 128, as shown in FIG. 8F.

For some applications (not shown), prosthesis 100 (described hereinabove with reference to any of FIGS. 1-6) is implanted transseptally. For such applications, the prosthesis is advanced via the femoral vein, into the right atrium. An incision is made in the septum of the heart to provide access to the left atrium. The prosthesis is then advanced through the incision in the septum and is implanted through a technique similar to the one described hereinabove with reference to FIGS. 8C-8F. Such a method typically includes some or all of the following: making an incision in a femoral vein; inserting a trocar through the incision in the femoral vein and advancing the trocar into the right atrium of the heart; making an incision in the septum of the heart; advancing the trocar through the incision in the septum of the heart and into the left atrium; advancing a mitral valve prosthesis through the trocar and into the left atrium of the heart; advancing the trocar past the native mitral valve and into the left ventricle of the heart; releasing the engagement arms from the trocar; retracting the trocar such that the engagement arms are placed around the outer surface of the native mitral valve leaflets; releasing the inner support structure from the trocar; closing the incision in the septum; and withdrawing the trocar from the heart.

Reference is now made to FIG. 9, which is a schematic illustration of implanted mitral valve prosthesis 100 (described hereinabove with reference to any of FIGS. 1-6), in accordance with some applications of the present invention. Mitral valve prosthesis 100 has engagement arms 106 that clamp leaflets of native valve 128. Typically, downstream ends of engagement arms define a rotational gap. When valve prosthesis 100 is implanted in the native mitral valve, the commissures of the native mitral valve, and the regions of the native leaflets adjacent to the commissures are squeezed within the gap between the two ends of outer engagement arms 106. The leaflets are squeezed within the gap such that the regions of the anterior and posterior leaflets that are adjacent to the commissures are squeezed against one another and seal the commisures.

Figure 10D:
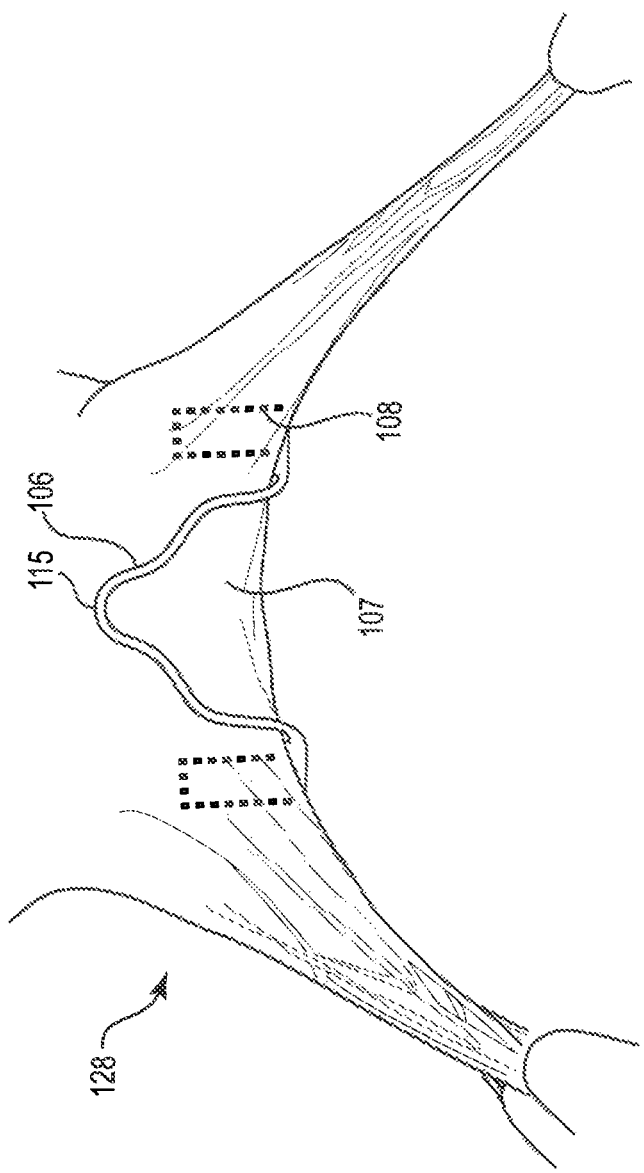

Reference is now made to FIGS. 10A-D, which are schematic illustrations of engagement arms 106 of mitral valve prosthesis 100, in accordance with respective applications of the present invention. In accordance with respective applications, engagement arms 106 form a U-shaped troughs 110 (FIG. 10A), circular-shaped troughs 111 (FIG. 10B), bulging flask-shaped troughs 113 (FIG. 10C), and/or undulating, bottle-nipple shaped trough 115 (FIG. 10D). For some applications (not shown), the engagement arms are shaped to include two or more parallel arches.

Figure 11A:
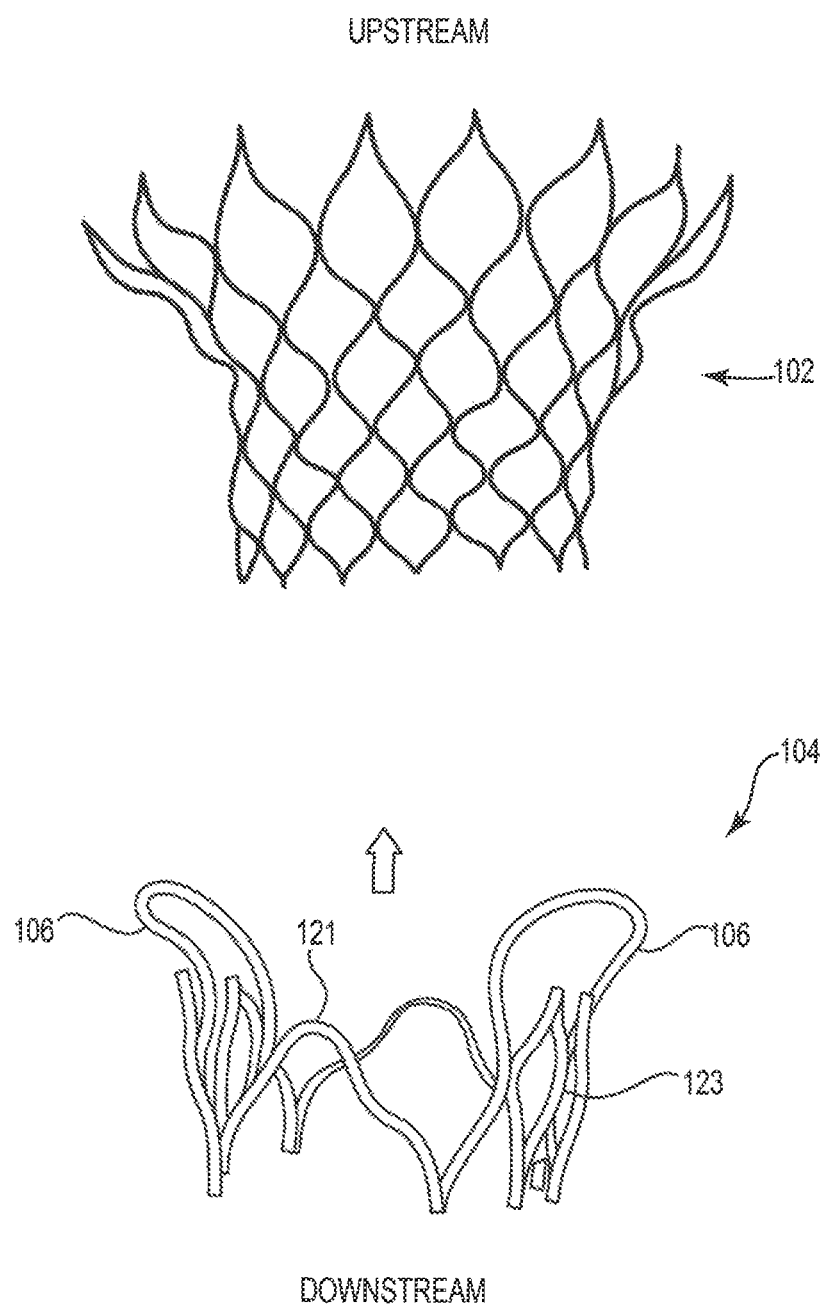
FIGS. 11A-D are schematic illustrations of an engagement arm assembly, in accordance with some applications of the present invention.
Figure 11B:
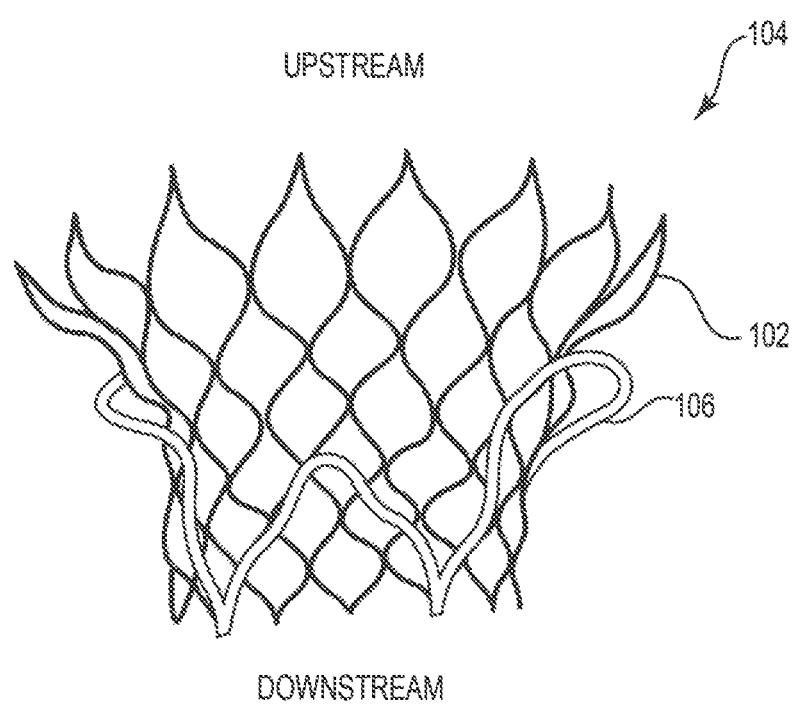

Reference is now made to FIGS. 11A-D, which are schematic illustrations of outer support structure 104, in accordance with some applications of the present invention. FIG. 11A shows a single continuous structure that includes engagement arms 106, the engagement arms emerging from respective points of a connecting frame 121 of the outer support structure. As shown in FIG. 11B, the outer support structure is placed over inner support structure 102, and is coupled to the inner support structure. For some applications, using a single continuous structure from which the engagement arms emerge ensures that the engagement arms are placed symmetrically on the prosthesis, facilitates assembly of the prosthesis, and/or enhances the overall frame strength of the prosthesis.

As shown in FIG. 11A, for some applications, the engagements arms include a leaflet capturing element 123 (e.g., additional struts, as shown) to facilitate the clamping of the native valve leaflets, thereby reducing motion of the native valve leaflets, immobilizing the native valve leaflets, and/or preventing systolic anterior motion of the leaflets. Typically, by preventing systolic anterior motion of the leaflets, the engagement arms prevent the native leaflets from blocking or interfering with the LVOT. For some applications, engagement arms 106, as described with reference to FIGS. 11A-D, or elsewhere in the present application, prevent systolic anterior motion of the native leaflets even in the absence of the leaflet capturing element or any other additional element.

Figure 11C:
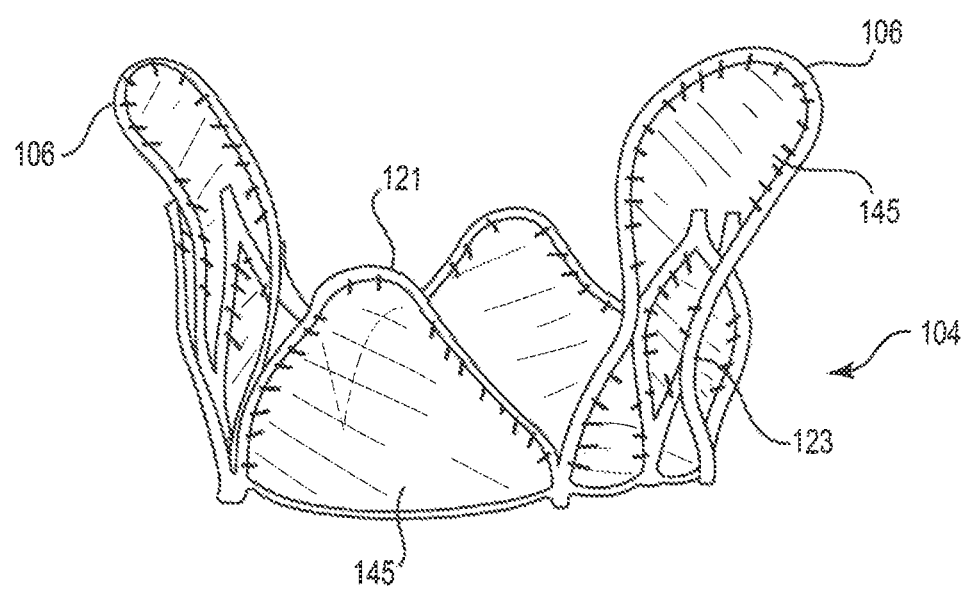
Figure 11D:
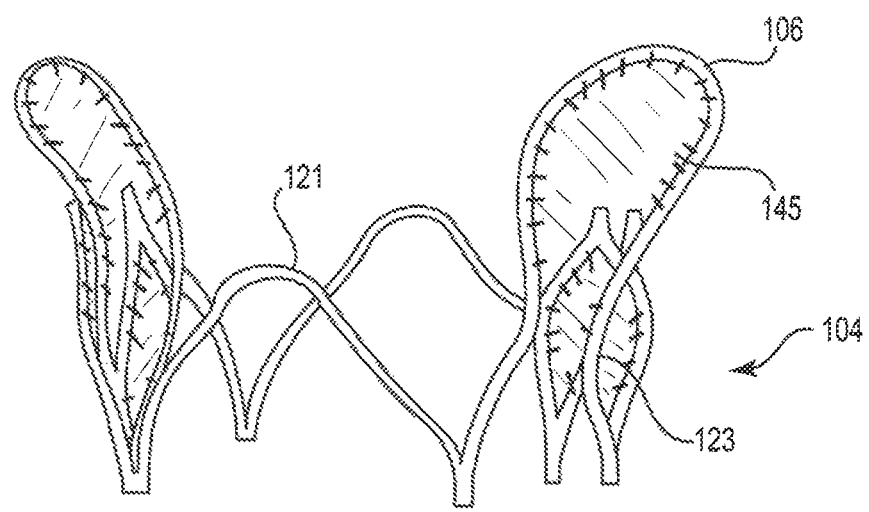

As shown in FIGS. 11C-D, for some applications, the whole of outer support structure 104 (FIG. 11C), or a portion thereof (FIG. 11D), is covered with a biocompatible cloth 145 (e.g., polyester). Typically, the cover helps to prevent systolic anterior motion of the native leaflets through engagement arms 106, and/or to reduce metal to metal abrasion between the outer and inner support structures. For some applications, the cover generally may help capture calcific, thrombotic, or other material which might be dislodged from the native valve or the surrounding tissue.

Figure 12:
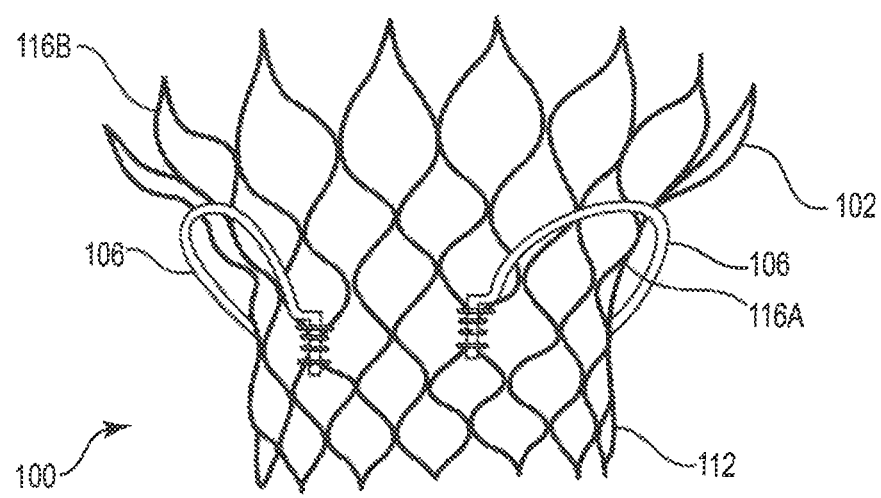
FIG. 12 is a schematic illustration of the mitral valve prosthesis, in accordance with some applications of the present invention.

Reference is now made to FIG. 12, which is a schematic illustration of the mitral valve prosthesis 100, in accordance with some applications of the present invention. Prosthesis 100, as shown in FIG. 12, is generally similar to prosthesis 100 described hereinabove, except that the downstream ends of engagement arms 106 of prosthesis 100 as shown in FIG. 12 are connected directly to inner support structure 102. As shown in FIG. 12, engagement arms 106 are attached to inner support structure 102 at downstream section 112 of the inner support structure. In accordance with some applications, engagement arms 106 are directly attached to inner support structure 102 at any suitable location, including but not limited to downstream section 112, intermediate section 116A, and/or upstream-most section 116B (the aforementioned sections typically being as described hereinabove with reference to FIG. 3). For some applications, the engagement arms are integrally formed with the inner support structure.

Figure 13:
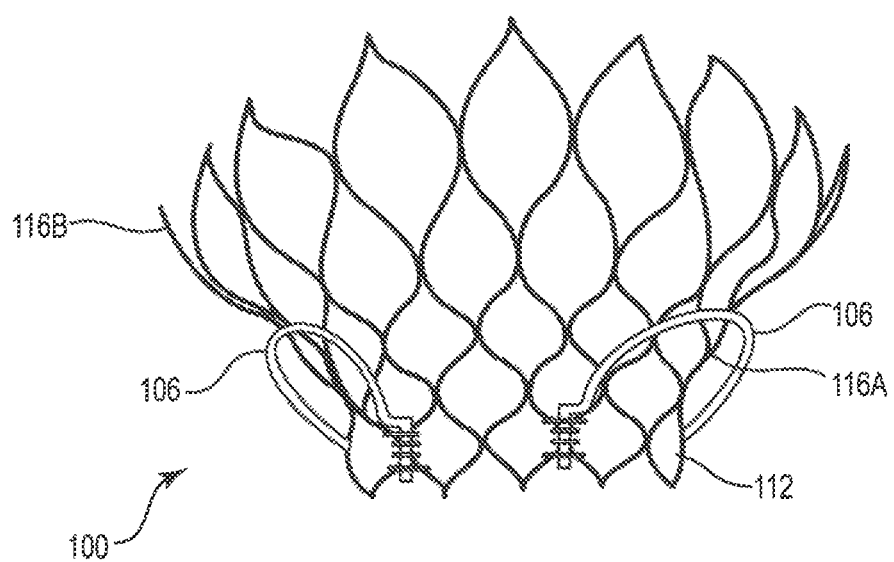
FIG. 13 is a schematic illustration of the mitral valve prosthesis, in accordance with some applications of the present invention.

Reference is now made to FIG. 13, which is a schematic illustration of mitral valve prosthesis 100, in accordance with some applications of the present invention. Prosthesis 100, as shown in FIG. 13, is generally similar to prosthesis 100 described with reference to FIG. 12. However, relative to the prosthesis shown in FIG. 12, the prosthesis shown in FIG. 13 includes a shorter downstream section 112 of more than 1 mm and/or less than 20 mm, e.g., 1-20 mm (for example, more than 10 mm and/or less than 14 mm, e.g., 10-14 mm). In addition, relative to the prosthesis shown in FIG. 12, engagement arms 106 of the prosthesis shown in FIG. 13 are attached to inner support structure 102 closer to the downstream end of the prosthesis. For some applications, use of a shorter prosthesis improves the maneuverability of the prosthesis when loaded on a delivery catheter, thereby facilitating implantation of such devices and reducing the time required to perform the implantation procedure, relative to the use of a longer prosthesis. For some applications, use of a shorter prosthesis reduces interference of the prosthesis with the left ventricular outflow tract (LVOT), relative to a longer prosthesis.

Figure 14A:
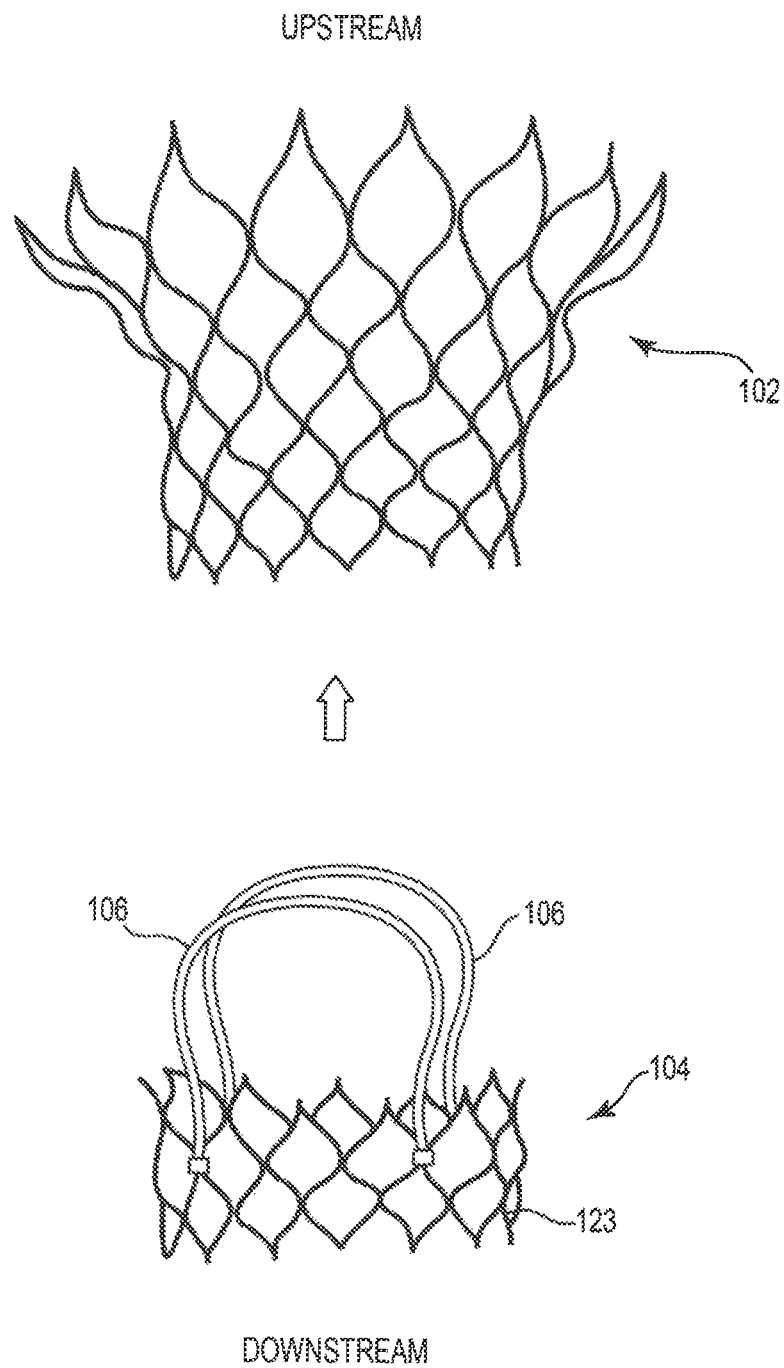
FIGS. 14A-B are schematic illustrations of the mitral valve prosthesis, in accordance with some applications of the present invention.
Figure 14B:
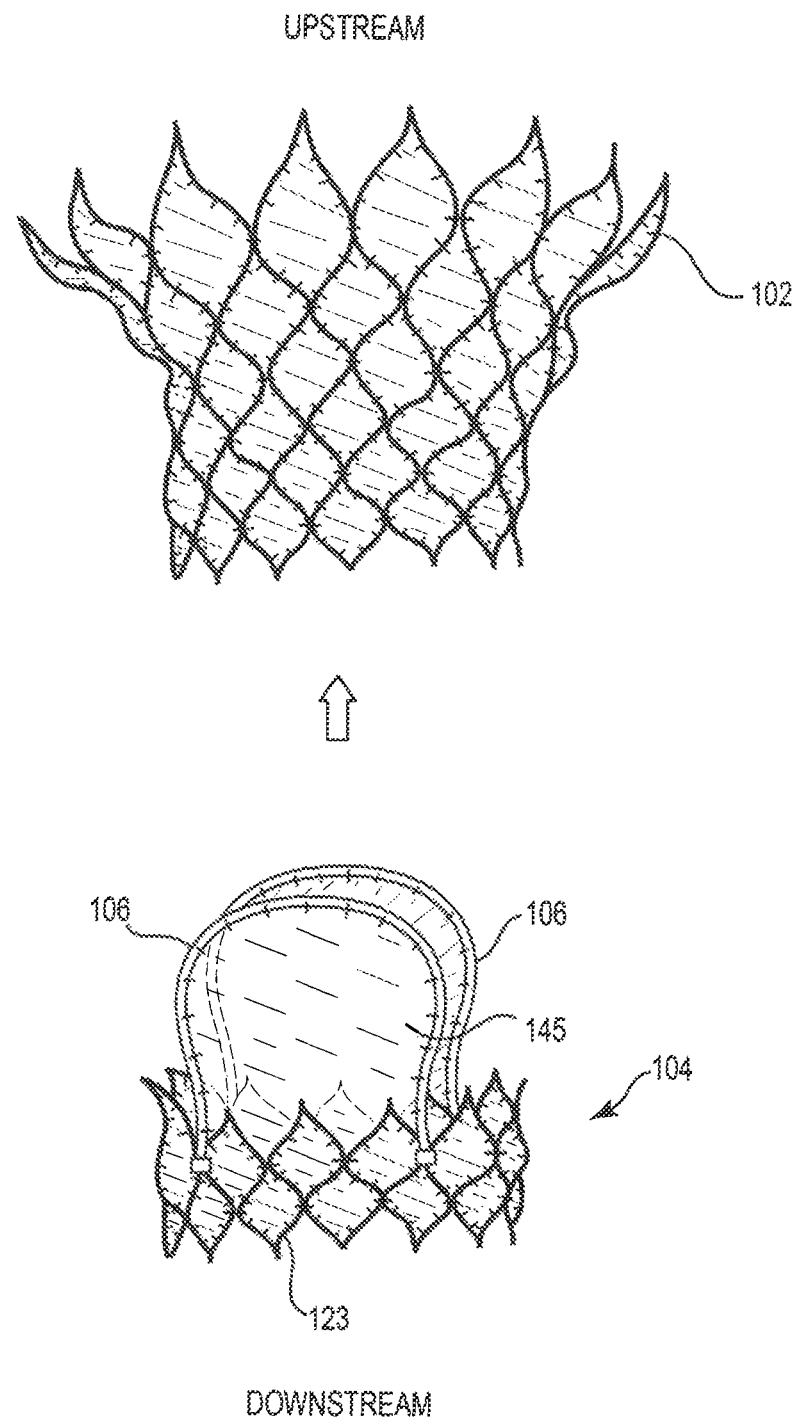

Reference is now made to FIGS. 14A-B, which are schematic illustrations of portions of mitral valve prosthesis 100, in accordance with some applications of the present invention. FIGS. 14A-B shows a single outer support structure 104 that includes engagement arms 106, the engagement arms emerging from respective points of the continuous structure. Connecting frame 123 of the outer support structure includes struts that are geometrically similar in structure to the corresponding struts on the inner support structure 102. For some applications, using struts that are similar to the corresponding struts on the inner support structure enhances the frame strength of the prosthesis, when the inner and outer support structures are coupled to one another.

In accordance with respective applications, engagement arms 106 are coupled to connecting frame 123 of outer support structure 104, or the engagement arms and the connecting frame form a single continuous structure. As described hereinabove with reference to FIGS. 11A-B, for some applications, using a single continuous structure from which the engagement arms emerge ensures that the engagement arms are placed symmetrically on the prosthesis, facilitates assembly of the prosthesis, and/or enhances the overall frame strength of the prosthesis.

As shown in FIG. 14B, for some applications, at least a portion of outer support structure 104 is covered with a biocompatible cloth 145 (e.g., polyester). Typically, the cover helps to prevent systolic anterior motion of the native leaflets through engagement arms 106, and/or to reduce metal to metal abrasion between the outer and inner support structures. For some applications, the cover generally may help capture calcific, thrombotic, or other material which might be dislodged from the native valve or the surrounding tissue.

Figure 15A:
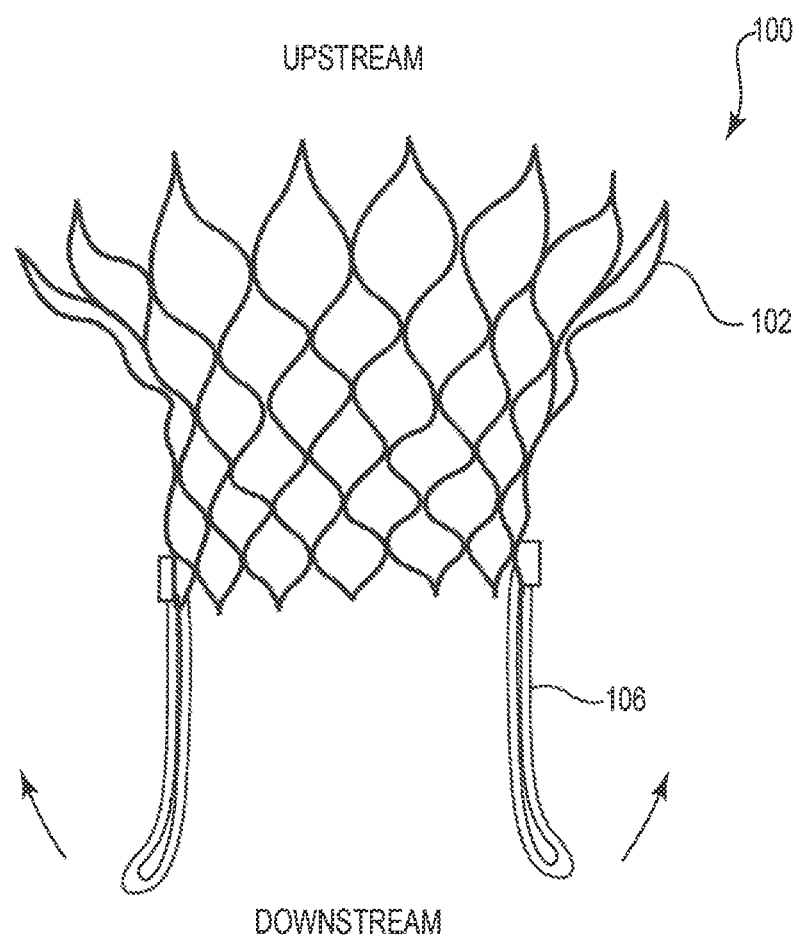
FIGS. 15A-B are schematic illustrations of the mitral valve prosthesis, in accordance with some applications of the present invention.
Figure 15B:
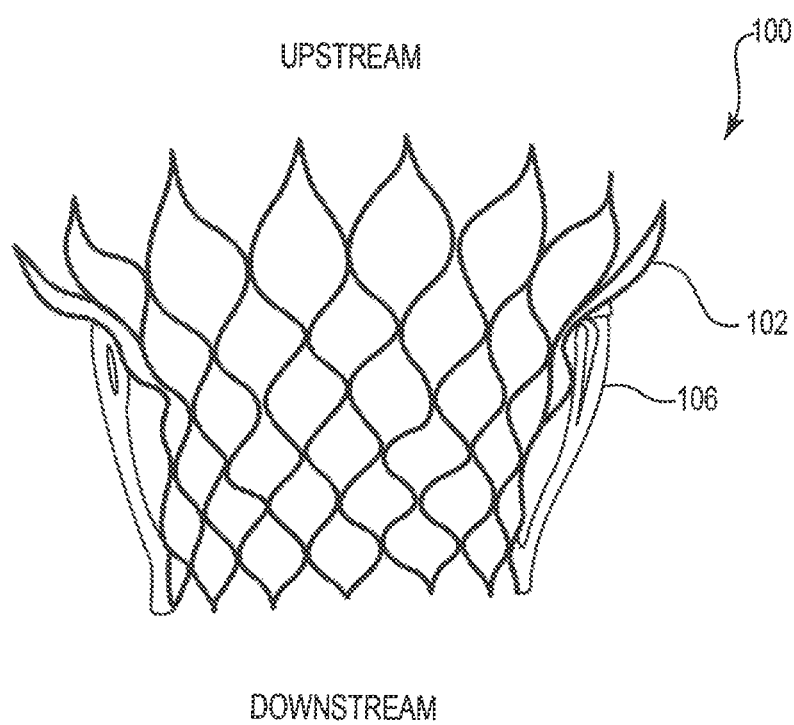

Reference is now made to FIGS. 15A-B, which are schematic illustrations of mitral valve prosthesis 100, in accordance with some applications of the present invention. For some applications, during the construction of the mitral valve prosthesis, engagement arms 106 are cut as integral parts of inner support structure 102. Engagement arms 106 are folded into position with respect to inner support structure 102 using heat treatment. FIG. 15B shows the engagement arms having been folded into position, with respect to the inner support structure.

Features of mitral valve prosthesis 100 described with reference to respective figures are not limited to the prostheses shown in those figures. Rather, features of the prosthesis shown in any of the figures could be used in combination with any of the other features described herein, mutatis mutandis. Examples of the features that may be combined with each other include, but are not limited to:

structures of the cells of inner support structure 102 asymmetrical engagement arms 106 of FIGS. 2A-D, the features of inner support structure 102 and outer support structure 104 described with reference to FIGS. 4A-F the features of inner support structure 102 described with reference to FIGS. 5A-B the asymmetric inner support structure, and fixation barbs of the inner support structure, as described with reference to FIGS. 6A-D features of the outer support structure, and/or the engagement arms described with reference to FIGS. 9-15B.

Further, any of the surgical techniques described herein can be used for implantation of prosthesis 100, including but not limited to, methods of implanting the mitral valve prosthesis transapically, transatrially, and transseptally, for example, as described hereinabove with reference to FIGS. 7-8.

As used herein, the terms "upstream" and "downstream" are used to refer to the upstream and downstream directions of the blood flow when mitral valve prosthesis 100 is implanted inside the subject's heart. The terms "upstream" and "downstream" should be interpreted as being interchangeable, respectively, with the terms "proximal" and "distal."

The techniques described herein may be combined with the techniques described in one or more of the following applications, all of which applications are incorporated herein by reference:

US 2008/0071368 to Tuval
US 2009/0281618 to Hill
US 2010-0036479 to Hill

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising a mitral valve prosthesis for implantation at a native mitral valve complex of a subject, the prosthesis comprising:
   an inner support structure having a downstream section, and an upstream section, wherein the upstream section has a cross-sectional area greater than the downstream section, the inner support structure being configured to be positioned at least partially on an atrial side of the native valve complex, and to apply an axial force directed toward a left ventricle; and
   an outer support structure having two or more engagement arms, a first engagement arm having a first length and a second engagement arm directly opposite the first engagement arm having a second length longer than the first length, wherein the engagement arms are coupled to the inner support structure, and
   wherein the first and second engagement arms are configured to clamp portions of leaflets of the native valve between the inner support structure and the engagement arms.

2. The apparatus according to claim 1, wherein the engagement arms are integrally formed with the inner support structure.

3. The apparatus according to claim 1, wherein the engagement arms comprise posterior and anterior engagement arms configured to clamp, respectively, posterior and anterior leaflets of the native mitral valve complex, and wherein a ratio of the length of the anterior engagement arm to the length of the posterior arm is between 1.1:1 and 15:1.

4. The apparatus according to claim 3, wherein the ratio is between 1.3:1 and 2:1.

5. The apparatus according to claim 3, wherein the length of the anterior engagement arm is between 2 mm and 35 mm.

6. The apparatus according to claim 5, wherein the length of the anterior engagement arm is between 15 mm and 25 mm.

7. The apparatus according to claim 3, wherein the length of the posterior engagement arm is between 2 mm and 35 mm.

8. The apparatus according to claim 7, wherein the length of the posterior engagement arm is between 7 mm and 23 mm.

9. The apparatus according to claim 1, wherein the outer support structure further comprises a connecting frame, the connecting frame of the outer support structure being configured to be coupled to the inner support structure.

10. The apparatus according to claim 9, wherein the inner support structure is shaped to define a plurality of cells, and wherein the connecting frame of the outer support structure is shaped to define a plurality of cells having shapes and sizes that match cells of the inner support structure.

11. The apparatus according to claim 1, wherein clamping of the leaflets reduces motion of the leaflets, by clamping portions of the leaflets between the inner support structure and the engagement arms.

12. The apparatus according to claim 11, wherein the prosthesis is configured to immobilize the native valve leaflets, by clamping the leaflets inside the engagement arms.

13. The apparatus according to claim 11, wherein the prosthesis is configured to prevent systolic anterior motion of the native valve leaflets, by clamping the leaflets inside the engagement arms.

14. The apparatus according to claim 11, wherein the prosthesis is configured to prevent the native leaflets from interfering with LVOT, by clamping the leaflets inside the engagement arms.

15. The apparatus according to claim 11, wherein the outer support structure further comprises covers for covering the engagement arms, the covers being configured to reduce the motion of the native leaflets.

16. The apparatus according to claim 1, further comprising a prosthetic valve that comprises prosthetic valve leaflets and that is coupled to the inner support structure, wherein the prosthesis is configured such that, upon implantation thereof:
   downstream ends of native valve leaflets of the native mitral valve complex,
   downstream ends of the engagement arms, and
   downstream ends of the prosthetic leaflets,
   are disposed at a longitudinal distance from one another of less than 3 mm, the longitudinal distance being measured in a direction of a longitudinal axis of the prosthesis.

17. The apparatus according to claim 16, wherein the downstream ends of the engagement arms are coupled to the inner support structure within 3 mm of a downstream end of the inner support structure.

18. The apparatus according to claim 16, wherein the prosthesis is configured such that, upon implantation thereof, no portion of the prosthesis protrudes into a left ventricle of the subject by more than 3 mm.

19. The apparatus according to claim 16, wherein the prosthesis is configured such that, upon implantation thereof:
   the downstream ends of native valve leaflets of the native mitral valve complex,
   the downstream ends of the engagement arms, and
   the downstream ends of the prosthetic leaflets,
   are disposed at a longitudinal distance from one another of less than 1 mm, the longitudinal distance being measured in a direction of a longitudinal axis of the prosthesis.

20. The apparatus according to claim 19, wherein the prosthesis is configured such that, upon implantation thereof, no portion of the prosthesis protrudes into a left ventricle of the subject by more than 1 mm.

21. The apparatus according to claim 19, wherein the downstream ends of the engagement arms are coupled to the inner support structure within 1 mm of a downstream end of the inner support structure.

22. The apparatus according to claim 1, wherein the engagement arms are configured to define first configurations thereof during implantation of the prosthesis, and to change shape so as to define second configurations thereof, subsequent to being placed over the native leaflets of the native mitral valve complex, each of the engagement arms spanning a width of less than 12 mm in the first configuration thereof, and spanning a width of more than 15 mm when in the second configuration thereof.

23. The apparatus according to claim 22, wherein, in the first configuration thereof, the engagement arms are configured to facilitate functioning of the native valve complex during implantation of the prosthesis.

24. The apparatus according to claim 22, wherein, in the first configuration thereof, the engagement arms are configured to fit between papillary muscles of the native valve complex.

25. The apparatus according to claim 22, wherein, in the first configuration thereof, the engagement arms are configured to span a width of less than 8 mm.

26. The apparatus according to claim 22, wherein, in the second configuration thereof, the engagement arms are configured to span a width of more than 35 mm.

27. The apparatus according to claim 1,
further comprising a prosthetic valve having prosthetic valve leaflets coupled to the inner support structure such that downstream ends of the prosthetic valve leaflets are within 3 mm of the downstream ends of the engagement arms,
wherein the engagement arms are coupled to the inner support structure at downstream ends of the engagement arms, and
wherein a longitudinal distance from a downstream end to an upstream end of each of the engagement arms is less than 18 mm, the longitudinal distance being measured in a direction of a longitudinal axis of the prosthesis.

28. The apparatus according to claim 27, wherein the prosthetic valve leaflets are coupled to the inner support structure such that downstream ends of the prosthetic valve leaflets are within 1 mm of the downstream ends of the engagement arms.

29. The apparatus according to claim 27, wherein the downstream ends of the engagement arms are coupled to the inner support structure within 3 mm of a downstream end of the inner support structure.

30. The apparatus according to claim 29, wherein the downstream ends of the engagement arms are coupled to the inner support structure within 1 mm of a downstream end of the inner support structure.

31. The apparatus according to claim 27, wherein the longitudinal distance from the downstream end to the upstream end of each of the engagement arms is less than 12 mm.

32. The apparatus according to claim 31, wherein the longitudinal distance from the downstream end to the upstream end of each of the engagement arms is less than 10 mm.

33. The apparatus according to claim 1, further comprising a prosthetic valve having prosthetic valve leaflets coupled to the inner support structure, the prosthesis being configured such that, upon implantation thereof:
downstream ends of native valve leaflets of the native mitral valve complex, and downstream ends of the engagement arms are disposed at a longitudinal distance from one another of less than 3 mm, the longitudinal distance being measured in a direction of a longitudinal axis of the prosthesis, and
a downstream end of the inner support structure and downstream ends of the prosthetic valve leaflets are at a longitudinal distance of at least 4 mm upstream of the downstream ends of the native valve leaflets, the longitudinal distance being measured in a direction of a longitudinal axis of the prosthesis.

34. The apparatus according to claim 33, wherein the prosthesis is configured such that, upon implantation thereof, the downstream end of the inner support structure and the downstream ends of the prosthetic valve leaflets are at a longitudinal distance of at least 10 mm upstream of the downstream ends of the native valve leaflets.

35. The apparatus according to claim 1, further comprising a prosthetic valve having prosthetic valve leaflets, the prosthetic valve leaflets being coupled to the inner support structure such that downstream ends of the prosthetic valve leaflets are at least 4 mm upstream of the downstream ends of the engagement arms.

36. The apparatus according to claim 35, wherein the prosthetic valve leaflets are coupled to the inner support structure such that the downstream ends of the prosthetic valve leaflets are at least 10 mm upstream of the downstream ends of the engagement arms.

* * * * *